United States Patent [19]

Kiefer et al.

[11] Patent Number: 5,428,139
[45] Date of Patent: Jun. 27, 1995

[54] BICYCLOPOLYAZAMACROCYCLOPHOS- PHONIC ACID COMPLEXES FOR USE AS RADIOPHARMACEUTICALS

[75] Inventors: Garry E. Kiefer, Lake Jackson; Jaime Simon, Angleton, both of Tex.

[73] Assignee: The Dow Chemical Company, Midland, Mich.

[21] Appl. No.: 806,069

[22] Filed: Dec. 10, 1991

[51] Int. Cl.$^6$ ............................................. C07F 13/00
[52] U.S. Cl. ........................................ 534/10; 534/14
[58] Field of Search ................. 424/1.1, 1.65; 534/10, 534/13, 14, 16; 540/472

[56] References Cited

U.S. PATENT DOCUMENTS

| | | | |
|---|---|---|---|
| 4,156,683 | 5/1979 | Lehn | 260/338 |
| 4,647,447 | 3/1987 | Gries et al. | 424/9 |
| 4,822,594 | 4/1989 | Gibby | 424/9 |
| 4,885,363 | 12/1989 | Tweedle et al. | 540/465 |
| 4,889,931 | 12/1989 | Rocklage et al. | 540/465 |
| 4,898,724 | 2/1990 | Simon et al. | 424/1.1 |
| 4,920,195 | 4/1990 | Kankare et al. | 534/16 |
| 4,923,985 | 5/1990 | Gansow et al. | 540/474 |
| 4,940,796 | 7/1990 | Mathias et al. | 546/323 |
| 5,026,802 | 6/1991 | Mathias et al. | 526/259 |
| 5,047,527 | 9/1991 | Handel et al. | 540/474 |
| 5,059,412 | 10/1991 | Simon et al. | 424/1.1 |
| 5,064,633 | 11/1991 | Simon et al. | 424/1.1 |

FOREIGN PATENT DOCUMENTS

| | | |
|---|---|---|
| 0238196 | 9/1987 | European Pat. Off. ..... A61K 49/00 |
| 0352218 | 1/1990 | European Pat. Off. ..... A61K 49/00 |
| 0391766 | 10/1990 | European Pat. Off. . |
| 438206 | 10/1990 | European Pat. Off. . |
| 0430863 | 6/1991 | European Pat. Off. . |
| 0438206 | 7/1991 | European Pat. Off. . |
| 3825040 | 1/1990 | Germany . |
| 9110669 | 10/1990 | WIPO . |
| 9110645 | 7/1991 | WIPO . |

OTHER PUBLICATIONS

Stetter et al., *Tetrahedron*, vol. 37 (1981) pp. 767–772.
Chemical Abstracts, vol. 95, (1981), p. 702, abstract No. 115487t.
Chemical Abstracts, vol. 100, (1984), p. 593, abstract No. 209772f.
Chemical Abstracts, vol. 110, (1989), p. 892, abstract No. 127400a.
Chemical Abstracts, vol. 111, (1989), p. 921, abstract No. 208180b.
Chemical Abstracts, vol. 113, (1990), p. 701, abstract No. 59139g.
Chemical Abstracts, vol. 115, (1991), p. 21, abstract No. 280870b.
Chemical Abstracts, vol. 115, (1991), p. 845, abstract No. 20829y.
Chemical Abstracts, vol. 116, (1992), p. 583, abstract No. 21083h.
Derwint Publications, Ltd, abstract No. 85–018012/03, 25 Mar. 1983.
Derwint Publications Ltd., abstract No. 87–229593/33, 23 Jan. 1986.
Derwint Publications, Ltd., abstract No. 87–250202/35, 13 Feb. 1986.
Derwint Publications, Ltd., abstract No. 90–307139/41 24 Mar. 1989.
Derwent Publications, Ltd., abstract No. 91–216892/30, 18 Jan. 1990.
Derwent Abstract No. 91–117221/16 For U.S. Pat. No. 7,498,320.
On Line Ref. From IFI Claims Database for U.S. Pat. No. 5,053,503 dated Jan. 1, 1991.
On Line Ref. From IFI Claims Database for U.S. Pat. No. 5,049,667, Sep. 17, 1991.

*Primary Examiner*—Philip Tucker
*Assistant Examiner*—Lara E. Chapman
*Attorney, Agent, or Firm*—Karen L. Kimble

[57] ABSTRACT

Complexes of bicyclopolyazamacrocyclophosphonic acid compounds with a metal ion, e.g. $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{99m}$Tc, $^{67}$Ga, $^{68}$Ga, $^{105}$Rh, $^{97}$Ru, $^{111}$In, $^{113m}$In or $^{115m}$In ion, are disclosed. The complexes can be covalently attached to a biologically active molecule, e.g. an antibody or antibody fragment, to form conjugates. The complexes and conjugates are useful as radiopharmaceutical agents for therapy and/or diagnostic purposes.

10 Claims, No Drawings

BICYCLOPOLYAZAMACROCYCLOPHOS-PHONIC ACID COMPLEXES FOR USE AS RADIOPHARMACEUTICALS

This invention concerns complexes that contain bicyclopolyazamacrocyclophosphonic acid ligands with metal ions, and conjugates thereof, for use as radiopharmaceuticals, especially for the treatment and/or diagnosis of cancer.

BACKGROUND OF THE INVENTION

The delivery of radionuclides to different organ and tissue targets has been the objective of many research efforts for both diagnostic and therapeutic purposes. Various molecules have been tried that would carry the active component to the desired site and yet be stable at least until the site has been reached by the delivery system. Halogenated (e.g. $^{131}$I and $^{88m}$Br) organic molecules have been used. Thus iodinated hippuran has been used to study renal function, e.g. *J. Nucl. Med.* 23, 377-380 (1982). Also labeling a monoclonal antibody with $^{131}$I has been proposed for the detection and therapy of cancer, e.g. *Cancer Res.* 44, 5744-5751 (1984).

Metallic radionuclides offer a variety of nuclear properties and chemistries. Thus, for example, $^{201}$Tl, $^{67}$Cu, $^{99m}$Tc, $^{90}$Y and various isotopes of In and Ga are only a few examples of radioisotopes that have been used for diagnostic imaging and/or therapy. Of these metals, the chemistry of $^{99m}$Tc has been explored the most for use as a radiopharmaceutical. For example, Tc-diphosphonates are used to image the skeletal system [see Subramanian et al., *Radiology* 149, 823-828 (1983)]. Loberg et al. [*J. Nucl. Med.* 16, 533 (1975)] were able to study liver function with lipophilic $^{99m}$Tc complexes in which the Tc existed in a +3 oxidation state and the overall charge of the iminodiacetic acid complex was −1. Deutsch et al. [*Science* 213, 85 (1981)] was able to prepare Tc complexes with As and P containing ligands that localized in the heart. These compounds contained a Tc(III) core with an overall charge of the complex of +1. Also Volkert et al. [*Int'l. J. Appl. Rad. Isotopes* 35, 467-470 (1974)] were successful in delivering Tc(III) to brain tissue.

However, since $^{99m}$Tc is a pure gemma emiter, it is limited only to diagnostic applications. Therefore, there has been a need for particle emitting radioisotope complexes and/or conjugates which would be useful in therapy. Deutsch et al. [Corina Int'l., Veronai and Raven Press, pp. 733-740 (1990)] have used the combination of $^{186}$Re and a diphosphonate to treat bone tumors. Also Simon et al. (U.S. Pat. No. 4,898,724) teach the use of $^{153}$Sm and other rare earth radionuclides in combination with aminophosphonic acids for the treatment of bone pain and tumors.

The development of bone metastasis is a common and often catastrophic event for a cancer patient. The pain, pathological fractures, frequent neurological deficits and forced immobility caused by these metastatic lesions significantly decrease the quality of life for the cancer patient. The number of patients that contract metastatic disease is large since nearly 50% of all patients who contract breast, lung or prostate carcinoma will eventually develop bone metastasis. Bone metastasis are also seen in patients with carcinoma of the kidney, thyroid, bladder, cervix and other tumors, but collectively, these represent less than 20% of patients who develop bone metastasis. Metastatic bone cancer is rarely life threatening and occasionally patients live for years following the discovery of the bone lesions. Initially, treatment goals center on relieving pain, thus reducing requirements for narcotic medication and increasing ambulation. Clearly, it is hoped that some of the cancers can be cured.

The use of radionuclides for treatment of cancer metastatic to the bone dates back to the early 1950's. It has been proposed to inject a radioactive particle-emitting nuclide in a suitable form for the treatment of calcific lesions. It is desirable that such nuclides be concentrated in the area of the bone lesion with minimal amounts reaching the soft tissue and normal bone. Radioactive phosphorus (P-32 and P-33) compounds have been proposed, but the nuclear and biolocalization properties limit the use of these compounds. (E. Kaplan, et al., *J. Nucl. Med.* 1(1), 1, (1960); U.S. Pat. No. 3,965,254).

Another attempt to treat bone cancer has been made using phosphorus compounds containing a boron residue. The compounds were injected into the body (intravenously) and accumulated in the skeletal system. The treatment area was then irradiated with neutrons in order to activate the boron and give a therapeutic radiation dose. (U.S. Pat. No. 4,399,817).

The use of Re-186 complexed with a diphosphonate has also been proposed. [L. Mathieu et al., *Int. J. Applied Rad. & Isotopes,* 30, 725-727 (1979); J. Weinenger, A. R. Ketring et al., *J. Nucl. Med.,* 24(5), P125 (1983)]. However, the preparation and purification needed for this complex limits its utility and wide application.

Strontium-89 has also been proposed for patients with metastatic bone lesions. However, the long half-life (50.4 days), high blood levels and low lesion to normal bone ratios limit the utility. [N. Firusian, P. Mellin, C. G. Schmidt, *J. Urology,* 116, 764 (1976); C. G. Schmidt, N. Firusian, *Int. J. Clin. Pharmacol.,* 93, 199-205, (1974)].

A palliative treatment of bone metastasis has been reported which employed I-131 labeled α-amino-(3-iodo-4-hydroxybenzylidene)diphosphonate [M. Eisenhut, *J. Nucl. Med.,* 25(12), 1356-1361 (1984)]. The use of radioiodine as a therapeutic radionuclide is less than desirable due to the well known tendency of iodine to localize in the thyroid. Eisenhut lists iodide as one of the possible metabolites of this compound.

The use of radionuclides for calcific tumor therapy or relief of bone pain is discussed in published European patent application 176,288, where the use of Sm-153, Gd-159, Ho-166, Lu-177 or Yb-175 complexed with a ligand such as ethylenediaminetetraacetic acid (EDTA) or hydroxyethylenediaminetriacetic acid (HEEDTA) is disclosed. A macrocyclic system having a 1,4,7,10-tetraazacyclododecane moiety complexed with Sm-153, Gd-159, Ho-166, Lu-177 or Yb-175 for calcific tumor therapy or relief of bone pain is discussed in U.S. Pat. No. 5,059,412 which complex is very stable and has a lower charge than the complex disclosed in published European patent application 176,288.

Functionalized chelants, or bifunctional coordinators, are known to be capable of being covalently attached to an antibody having specificity for cancer or tumor cell epitopes or antigens. Radionuclide complexes of such antibody/chelant conjugates are useful in diagnostic and/or therapeutic applications as a means of conveying the radionuclide to a cancer or tumor cell. See, for example, Meares et al., *Anal. Biochem.* 142, 68-78, (1984); and Krejcarek et al., *Biochem. and Biophys. Res. Comm.* 77, 581-585 (1977).

Aminocarboxylic acid chelating agents have been known and studied for many years. Typical of the aminocarboxylic acids are nitrilotriacetic acid (NTA), ethylenediaminetetraacetic acid (EDTA), hydroxyethylethylenediaminetriacetic acid (HEDTA), diethylenetriaminepentaacetic acid (DTPA), trans-1,2-diaminocyclohexanetetraacetic acid (CDTA) and 1,4,7,10-tetraazacyclododecanetetraacetic acid (DOTA). Numerous bifunctional chelating agents based on aminocarboxylic acids have been proposed and prepared. For example the cyclic dianhydride of DTPA [Hnatowich et al. Science 220, 613-615, (1983); U.S. Pat. No. 4,479,930] and mixed carboxycarbonic anhydrides of DTPA [Gansow, U.S. Pat. Nos. 4,454,106 and 4,472,509; Krejcarek et al., Biochem. and Biophys. Res. Comm. 77, 581-585, (1977)] have been reported. When the anhydrides are coupled to proteins the coupling proceeds via formation of an amide bond thus leaving four of the original five carboxymethyl groups on the diethylenetriamine (DETA) backbone [Hnatowich et al. Int. J. Appl. Isot. 33, 327-332, (1982)]. In addition, U.S. Pat. Nos. 4,432,907 and 4,352,751 disclose bifunctional chelating agents useful for binding metal ions to "organic species such as organic target molecules or antibodies." As in the above, coupling is achieved via an amide group through the utilization of diaminotetraacetic acid dianhydrides. Examples of anhydrides include dianhydrides of EDTA, CDTA, propylenediaminetetraacetic acid and phenylene 1,2-diaminetetraacetic acid. A recent U.S. Pat. No. 4,647,447 discloses several complex salts formed from the anion of a complexing acid for use in various diagnostic techniques. Conjugation via a carboxyl group of the complexing acid is taught which gives a linkage through an amide bond.

In the J. Radioanal. Chem. 57(12), 553-564 (1980), Paik et al. disclose the use of p-nitrobenzylbromide in a reaction with a "blocked" diethylenetriamine, i.e. bis-(2-phthalimidoethyl)amine followed by deblocking procedures and carboxymethylation using chloroacetic acid, to give N'-p-nitrobenzyldiethylenetriamine N,N,N''',N''-tetraacetic acid. Again, since the attachment is through a nitrogen, a tetraacetic acid derivative is obtained. Conjugation of the bifunctional chelating agent and chelation with indium is discussed. Substitution on the nitrogen atom is also taught by Eckelman, et al. in the J. Pharm. Sci. 64(4), 704-706 (1975) by reacting amines such as "ethylenediamine or diethylenetriamine with the appropriate alkyl bromide before carboxymethylation." The compounds are proposed as potential radiopharmaceutical imaging agents.

Another class of bifunctional chelating agents based on aminocarboxylic acid functionality is also well documented in the literature. Thus, Sundberg, Meares, et al. in the J. Med. Chem. 17(12), 1304 (1974), disclosed bifunctional analogs of EDTA. Representative of these compounds are 1-(p-aminophenyl)-ethylenediaminetetraacetic acid and 1-(p-benzenediazonium)ethylenediaminetetraacetic acid. Coupling to proteins through the para-substituent and the binding of radioactive metal ions to the chelating group is discussed. The compounds are also disclosed in Biochem. and Biophys. Res. Comm. 75(1), 149 (1977), and in U.S. Pat. Nos. 3,994,966 and 4,043,998. It is important to note that the attachment of the aromatic group to the EDTA structure is through a carbon of the ethylenediamine backbone. Optically active bifunctional chelating agents based on EDTA, HEDTA and DTPA are disclosed in U.S. Pat. No. 4,622,420. In these compounds an alkylene group links the aromatic group (which contains the functionality needed for attachment to the protein) to the carbon of the polyamine which contains the chelating functionality. Other references to such compounds include Brechbiel et al., Inorg. Chem. 25, 2772-2781 (1986), U.S. Pat. No. 4,647,447 and International Patent Publication No. WO 86/06384.

More recently, certain macrocyclic bifunctional chelating agents and the use of their copper chelate conjugates for diagnostic or therapeutic applications have been disclosed in U.S. Pat. No. 4,678,667 and by Moi et al., Inorg. Chem. 26, 3458-3463 (1987). Attachment of the aminocarboxylic acid functionality to the rest of the bifunctional chelating molecule is through a ring carbon of the cyclic polyamine backbone. Thus, a linker, attached at one end to a ring carbon of the cyclic polyamine, is also attached at its other end to a functional group capable of reacting with the protein.

Another class of bifunctional chelating agents, also worthy of note, consists of compounds wherein the chelating moiety, i.e. the aminocarboxylic acid, of the molecule is attached through a nitrogen to the functional group of the molecule containing the moiety capable of reacting with the protein. As an example, Mikola et al. in patent application (WO 84/03698, published Oct. 27, 1984) disclose a bifunctional chelating agent prepared by reacting p-nitrobenzylbromide with DETA followed by reaction with bromoacetic acid to make the aminocarboxylic acid. The nitro group is reduced to the corresponding amine group and is then converted to the isothiocyanate group by reaction with thiophosgene. These compounds are bifunctional chelating agents capable of chelating lanthanides which can be conjugated to bio-organic molecules for use as diagnostic agents. Since attachment of the linker portion of the molecule is through one of the nitrogens of the aminocarboxylic acid, then one potential aminocarboxyl group is lost for chelation. Thus, a DETA-based bifunctional chelant containing four (not five) acid groups is prepared. In this respect, this class of bifunctional chelant is similar to those where attachment to the protein is through an amide group with subsequent loss of a carboxyl chelating group.

Recently Carney, Rogers, and Johnson disclosed (3rd. Int'l. Conf. on Monoclonal Antibodies for Cancer: San Diego, Calif.—Feb. 4-6, 1988) abstracts entitled "Absence of Intrinsically Higher Tissue Uptake from Indium-111 Labeled Antibodies: Co-administration of Indium 111 and Iodine-125 Labeled B72.3 in a Nude Mouse Model" and "Influence of Chelator Denticity on the Biodistribution of Indium-111 Labeled B72.3 Immunoconjugates in Nude Mice". The biodistribution of indium-111 complexed with an EDTA and DTPA bifunctional chelating agent is disclosed. Attachment of the aromatic ring to the EDTA/DTPA moieties is through an acetate methylene. Also at a recent meeting D. K. Johnson et al. [Florida Conf. on Chem. in Biotechnology, Apr. 26-29 (1988), Palm Coast, Fla.] disclosed bifunctional derivatives of EDTA and DTPA where a p-isothiocyanatobenzyl moiety is attached at the methylene carbon of one of the carboxymethyl groups. Previously Hunt et al. in U.S. Pat. Nos. 4,088,747 and 4,091,088 (1978) disclosed ethylenediaminediacetic acid (EDDA) based chelating agents wherein attachment of an aromatic ring to the EDDA moiety is through the alkylene or acetate methylene. The compounds are taught to be useful as chelates for studying hepatobiliary function. The preferred metal is technetium-99m. Indium-111 and indium-113m are also taught as useful radionuclides for imaging.

Such uses of other complexes are known using radio frequency to induce hyperthermia (Japanese Kokai Tokkyo Koho JP 61, 158,931) and fluorescent-Immuno-guided therapy (FIGS) [K. Pettersson et a., *Clinical Chem.* 29(1), 60–64 (1983) and C. Meares et al., *Acc. Chem. Res.* 17, 202–209 (1984)].

Consequently, it would be advantageous to provide a complex that does not readily dissociate, that exhibits rapid whole body clearance except from the desired tissue, and conjugates with an antibody to produce the desired results.

SUMMARY OF THE INVENTION

The present invention provides a new type of a stable metal complex, especially with metals that are rare earths or pseudo-rare earths in their chemistry. This invention teaches the use of these complexes and that the variance of their charge and lypophilic character may favorably alter their biodistribution when introduced into an animal. The conjugates of these complexes with a biologically active material, such as an antibody, are also a part of this invention. These complexes and conjugates may be formulated with suitable pharmaceutical carriers and administered to a mammal for diagnosis and/or therapy.

The present invention is directed to novel complexes which have a ligand that is a bicyclopolyazamacrocyclophosphonic acid compound of the formula

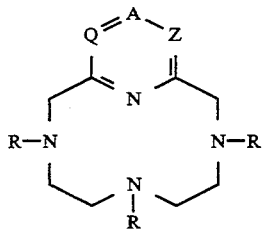

(I)

wherein:

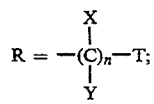

where:

X and Y are independently H, OH, $C_1$-$C_3$ alkyl or COOH;

n is an integer of 1, 2 or 3;

with the proviso that: when n is 2, then the sum of X and Y must equal two or more H; and when n is 3, then the sum of X and Y must equal three or more H; T is H, $C_1$-$C_{18}$ alkyl, COOH, OH, $SO_3H$,

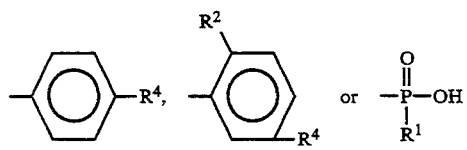

where:

$R^1$ is —OH, $C_1$-$C_5$ alkyl or —O—($C_1$-$C_5$ alkyl);

$R^4$ is H, $NO_2$, $NH_2$, isothiocyanato, semicarbazido, thiosemicarbazido, maleimido, bromoacetamido or carboxyl;

$R^2$ is H or OH; with the proviso that when $R^2$ is OH, then the R term containing the $R^2$ must have all X and Y equal to H;

with the proviso that at least one T must be $P(O)R^1OH$ and with the proviso that when one T is

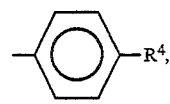

then one X or Y of that R term may be COOH and all other X and Y terms of that R term must be H;

A is CH, N, C—Br, C—Cl, C—$OR^3$, C—$OR^8$, $N^+$—$R^5$ $X^-$,

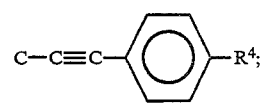

$R^3$ is H, $C_1$-$C_5$ alkyl, or benzyl substituted with at least one $R^4$;

$R^4$ is defined as above;

$R^5$ is $C_1$-$C_{16}$ alkyl, benzyl, or benzyl substituted with at least one $R^4$;

$R^8$ is $C_1$-$C_{16}$ alkylamino;

$X^-$ is $Cl^-$, $Br^-$, $I^-$ or $H_3CCO_2^-$;

Q and Z independently are CH, N, $N^+$—$R^5$ $X^-$, C—$CH_2$—$OR^3$ or C—C(O)—$R^6$;

$R^3$ and $R^5$ are defined as above;

$R^6$ is —O—($C_1$-$C_3$ alkyl), OH or $NHR^7$;

$R^7$ is $C_1$-$C_5$ alkyl or a biologically active material;

$X^-$ is defined as above; or pharmaceutically-acceptable salts thereof;

with the proviso that:
a) when Q, A or Z is N or $N^+$—$R^5$ $X^-$, then the other two groups must be CH;
b) when A is C—Br, C—Cl, C—$OR^3$ or C—$OR^8$, then both Q and Z must be CH;
c) the sum of the $R^4$, $R^7$ and $R^8$ terms, when present, may not exceed one; and
d) only one of Q or Z can be C—C(O)—$R^6$ and when one of Q or Z is C—C(O)—$R^6$, then A must be CH; and complexed with a metal ion of $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{99m}$Tc, $^{67}$Ga, $^{68}$Ga, $^{105}$Rh, $^{97}$Ru, $^{111}$In, $^{113m}$In or $^{115m}$In.

The complexes of Formula (I) use various metal ions, usually in the +3 state, selected from: samarium ($^{153}$Sm), lutetium ($^{177}$Lu), holmium ($^{166}$Ho), yttrium ($^{90}$Y), scandium ($^{47}$Sc), rhenium ($^{186}$Re) or ($^{188}$Re), praseodymium ($^{142}$Pr), technetium ($^{99m}$Tc), gallium ($^{67}$Ga) or ($^{68}$Ga), or indium ($^{111}$In) or ($^{115m}$In); with $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{142}$Pr, $^{99m}$Tc, $^{67}$Ga, $^{68}$Ga, $^{111}$In, $^{113m}$In or $^{115m}$In being preferred; with $^{153}$Sm, $^{177}$Lu, $^{166}$Ho, $^{90}$Y, $^{99m}$Tc, $^{67}$Ga, $^{68}$Ga, $^{111}$In, $^{113m}$In or $^{115m}$In being especially preferred; and with $^{153}$Sm, $^{177}$Lu or $^{166}$Ho being most preferred.

Complexes having gamma emissions, such as $^{99m}$Tc, $^{68}$Ga, $^{67}$Ga, $^{111}$In, $^{113m}$In, or $^{97}$Ru, are useful as diagnostic agents. Complexes having particle emissions, such as $^{149}$Pm, $^{142}$Pr, $^{90}$Y, or $^{175}$Yb, are useful as therapeutic agents. Complexes having both gamma and particle emissions, such as $^{153}Sm$, $^{177}Lu$, $^{159}Gd$, $^{140}La$, $^{166}Ho$, $^{47}Sc$, $^{186}Re$, $^{188}Re$, $^{105}Rh$, or $^{115m}In$, are useful as both diagnostic and therapeutic agents. The complexes so formed can be used by themselves or can be attached, by being covalently bonded, to an antibody or fragment thereof and used for diagnostic or therapeutic purposes. Such conjugates and complexes are useful as diagnostic and/or therapeutic agents.

Particularly preferred are those complexes of Formula (I) where:

X and Y are H;
n is 1; or
A, Q and Z are CH.

Bifunctional complexes of Formula (I) are desirable to prepare the conjugates of this invention. Such complexes contain a ligand which must have:

one R term where the T moiety is

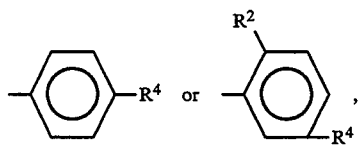

where $R^2$ and $R^4$ are defined as above, especially where in the two R terms not containing an $R^4$ term, both T terms are $P(O)R^1OH$, where $R^1$ is defined as above or where in the two R terms not containing an $R^4$ term, one T term is a COOH and the other T term is $P(O)R^1OH$, where $R^1$ is defined as above; preferably that moiety of the above T term where one of X or Y of that term is COOH; and also preferred are those ligands where n is 1 and/or the remaining X and Y terms are H; or A is $C-OR^3$ or $C-OR^8$, where $R^3$ and $R^8$ are defined as above or

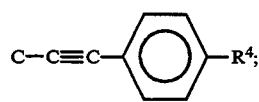

where $R^4$ is defined as above; or

A is CH, and one of Q or Z is CH and the other is $C-C(O)-R^6$, where $R^6$ is defined as above; especially those ligands where $R^6$ is $NHR^7$, where $R^7$ is a biologically active material.

Use of the complexes or conjugates of this invention for diagnosis or therapy of disease states such as cancer is possible.

The complexes and conjugates of this invention can be designed to provide a specific overall charge which advantageously influences the in vivo biolocalization. For example, when the metal ion is +3 the following can be obtained:

an overall charge of −2 or more—when
in three R terms T is $P(O)R^1OH$, where $R^1$ is OH, and n is 1;
in two R terms T is $P(O)R^1OH$, where $R^1$ is OH, in the third R term T is COOH, and n is 1;
in two R terms T is $P(O)R^1OH$, where $R^1$ is OH, in the third R term T is $P(O)R^1OH$, where $R^1$ is $C_1$-$C_5$ alkyl, and n is 1; or in two R terms T is $P(O)R^1OH$, where $R^1$ is OH, in the third R term T is $P(O)R^1OH$, where $R^1$ is $-O-(C_1$-$C_5$ alkyl), and n is 1;

an overall charge of −1—when
in one R term T is $P(O)R^1OH$, where $R^1$ is OH, and in the other two R terms T is $P(O)R^1OH$, where $R^1$ is $-O-(C_1$-$C_5$ alkyl), and n is 1;
in one R term T is $P(O)R^1OH$, where $R^1$ is OH, and in the other two R terms T is $P(O)R^1OH$, where $R^1$ is $C_1$-$C_5$ alkyl, and n is 1; or
in one R term T is $P(O)R^1OH$, where $R^1$ is OH, and in the other two R terms T is COOH, and n is 1;

an overall neutral charge—when
in the three R terms T is $P(O)R^1OH$, where $R^1$ is $-O-(C_1$-$C_5$ alkyl), and n is 1; or
in the three R terms T is $P(O)R^1OH$, where $R^1$ is $C_1$-$C_5$ alkyl, and n is 1; or an overall charge of +1—when
one of A, Q or Z is $N^+-R^5 X^-$, where $R^5$ and $X^-$ are defined as above; and in one R term, the T moiety is $P(O)R^1OH$, where $R^1$ is $C_1$-$C_5$ alkyl or $-O-(C_1$-$C_5$ alkyl); and in the other two R terms, the T moiety is COOH or $P(O)R^1OH$, where $R^1$ is $C_1$-$C_5$ alkyl or $-O-(C_1$-$C_5$ alkyl); and all X and Y terms are H.

Both the complexes and conjugates may be formulated to be in a pharmaceutically acceptable form for administration to an animal.

Use of the complexes and conjugates of this invention with other metal ions for use as contrast agents, such as for magnetic resonance imaging, is possible. The use of those complexes and conjugates is discussed in copending U.S. patent application Ser. No. 805,551, filed Dec. 10, 1991, now abandoned filed on even date herewith and entitled "Bicyclopolyazamacrocyclophosphonic Acid Complexes, and Conjugates Thereof, for Use as Contrast Agents" by G. E. Kiefer, J. R. Garlich and J. Simon (Attorney Docket No. C-38,662), the disclosure of which is hereby incorporated by reference.

DETAILED DESCRIPTION OF THE INVENTION

The complexes of this invention contain a ligand of Formula (I) which is numbered for nomenclature purposes as follows:

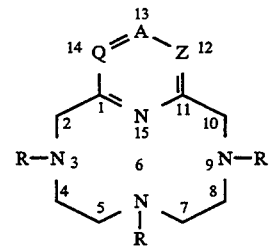

The present invention concerns development of radiopharmaceutical agents having synthetic modifications to the chelate enabling site specific delivery of the radiopharmaceutical agent to a desired tissue. The advantage being increased delivery of the radiopharmaceutical agent in the areas of interest based upon tissue affinity. The specificity of the complex of Formula (I) may be controlled by adjusting the total charge and lipophilic character of the complex. The overall range of the charge of the complex is from −3 to +1. For example, for a complex having 2 or more $PO_3H_2$ groups, the overall charge is highly negative and bone uptake is expected; whereas when the overall charge of the complex is 0 (thus neutral), the complex may have the ability to cross the blood brain barrier and normal brain uptake may be possible.

Tissue specificity may also be realized by ionic or covalent attachment of the chelate to a naturally occurring or synthetic molecule having specificity for a desired target tissue. One possible application of this approach is through the use of chelate conjugated monoclonal antibodies which would transport the radioactive chelate to diseased tissue enabling diagnosis and therapy.

Additionally, the present radiopharmaceutical agents of Formula (I) which are neutral in charge are particularly preferred for forming the conjugates of this invention since undesirable ionic interactions between the chelate and protein are minimized which preserves the antibody immunoreactivity.

While not wishing to be bound by theory, it is believed that when a charged complex of the invention is made (e.g. possibly −2 or −3 for bone, −1 for liver, or +1 for heart), the variations in that chelate ionic charge can influence biolocalization. Thus, if the antibody or other directing moiety is also specific for the same site, then the conjugate displays two portions to aid in site specific delivery.

The terms used in Formula (I) and for this invention are further defined as follows. "$C_1$–$C_3$ alkyl", "$C_1$–$C_5$ alkyl", "$C_1$–$C_{18}$ alkyl", include both straight and branched chain alkyl groups. An "animal" includes a warm-blooded mammal, preferably a human being.

"Biological active material" refers to, for example, a dextran, peptide, or molecules that have specific affinity for a receptor, or preferably antibodies or antibody fragments.

"Antibody" refers to any polyclonal, monoclonal, chimeric antibody or heteroantibody, preferably a monoclonal antibody; "antibody fragment" includes Fab fragments and F(ab')$_2$ fragments, and any portion of an antibody having specificity toward a desired epitope or epitopes. When using the term "radioactive metal chelate/antibody conjugate" or "conjugate", the "antibody" is meant to include whole antibodies and/or antibody fragments, including semisynthetic or genetically engineered variants thereof. Preferred antibodies are 1116-NS-19-9 (anti-colorectal carcinoma), 1116-NS-3d (anti-CEA), 703D4 (anti-human lung cancer), 704A1 (anti-human lung cancer) and B72.3. The hybridoma cell lines 1116-NS-19-9, 1116-NS-3d, 703D4, 704A1 and B72.3 are deposited with the American Type Culture Collection, having the accession numbers ATCC HB 8059, ATCC CRL 8019, ATCC HB 8301, ATCC HB 8302 and ATCC HB 8108, respectively.

As used herein, "complex" refers to a complex of the compound of the invention, e.g. Formula (I), complexed with a metal ion, where at least one metal atom is chelated or sequestered; "conjugate" refers to a metal ion conjugate that is covalently attached to an antibody or antibody fragment. The terms "bifunctional coordinator", "bifunctional chelating agent" and "functionalized chelant" are used interchangeably and refer to compounds that have a chelant moiety capable of chelating a metal ion and a moiety covalently bonded to the chelant moiety that is capable of serving as a means to covalently attach to an antibody or antibody fragment.

The bifunctional chelating agents described herein (represented by Formula I) can be used to chelate or sequester the metal ions so as to form metal ion chelates (also referred to herein as "complexes"). The complexes, because of the presence of the functionalizing moiety (represented by $R^4$ or $R^8$ in Formula I), can be covalently attached to biologically active materials, such as dextran, molecules that have specific affinity for a receptor, or preferably covalently attached to antibodies or antibody fragments. Thus the complexes described herein may be covalently attached to an antibody or antibody fragment or have specific affinity for a receptor and are referred to herein as "conjugates".

As used herein, "pharmaceutically-acceptable salt" means any salt or mixtures of salts of a complex or conjugate of formula (I) which is sufficiently non-toxic to be useful in therapy or diagnosis of animals, preferably mammals. Thus, the salts are useful in accordance with this invention. Representative of those salts formed by standard reactions from both organic and inorganic sources include, for example, sulfuric, hydrochloric, phosphoric, acetic, succinic, citric, lactic, maleic, fumaric, palmitic, cholic, palmoic, mucic, glutamic, gluconic, d-camphoric, glutaric, glycolic, phthalic, tartaric, formic, lauric, steric, salicylic, methanesulfonic, benzenesulfonic, sorbic, picric, benzoic and cinnamic acids and other suitable acids. Also included are salts formed by standard reactions from both organic and inorganic sources such as ammonium, alkali metal ions, alkaline earth metal ions, and other similar ions. Particularly preferred are the salts of the complexes or conjugates of formula (I) where the salt is potassium, sodium or ammonium. Also included are mixtures of the above salts.

DETAILED DESCRIPTION OF THE PROCESS

The ligands for the complex or conjugate of Formula (I) are prepared by various processes. Typical general synthetic approaches to such processes are provided by the reaction schemes given below.

In Scheme 1, the ligands of Formula (I) are prepared wherein X and Y=H, n=1 (but would also apply if n=2 or 3 with the corresponding change in the reagent), R has T=PO$_3$H$_2$, and Q, A and Z=CH.

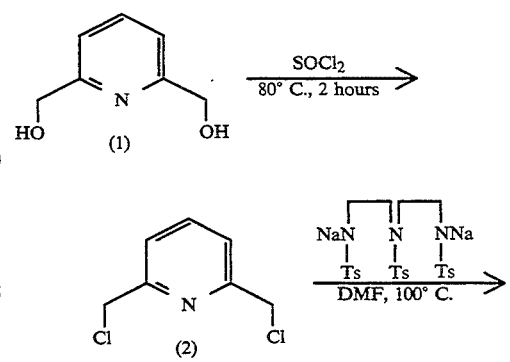

11

-continued
Scheme 1

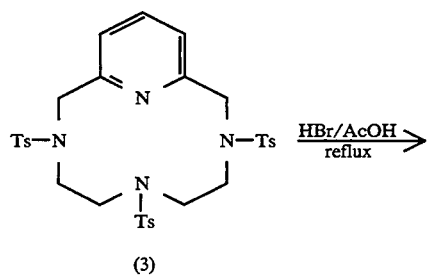

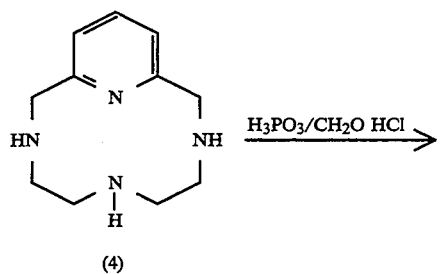

12

-continued
Scheme 1

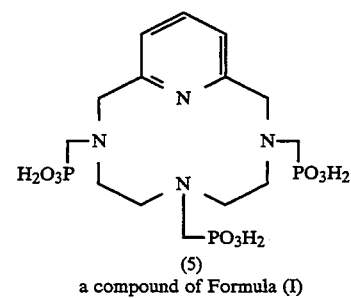

Scheme 2 prepares the compounds of Formula (I) wherein X and Y=H, n=1 (but would also apply if n=2 or 3 with the corresponding change in the reagent), and R has T=

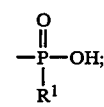

where $R^1$=—O—($C_1$-$C_5$ alkyl); and Q, A, and Z=CH.

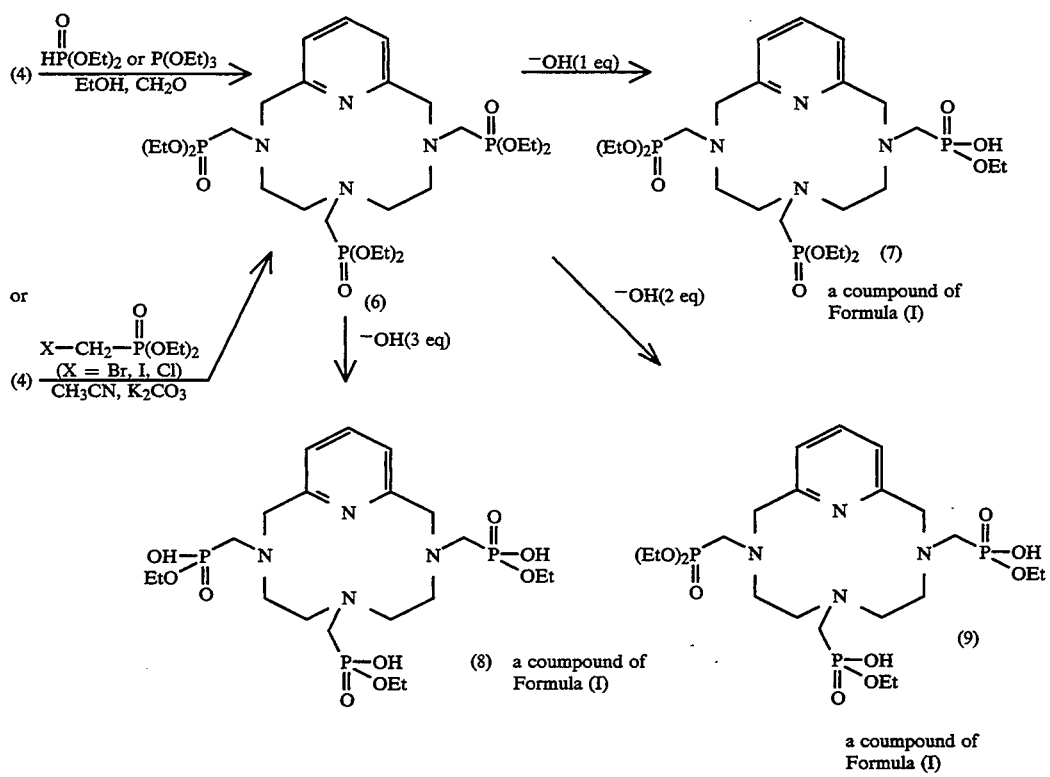

Scheme 3 prepares the compounds of Formula (I) wherein X and Y=H, n=1 (but would also apply if n=2 or 3 with the corresponding change in the reagent), R has T=

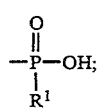
where $R^1 = C_1-C_5$ alkyl; and Q, A and Z=CH.
Scheme 3
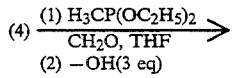
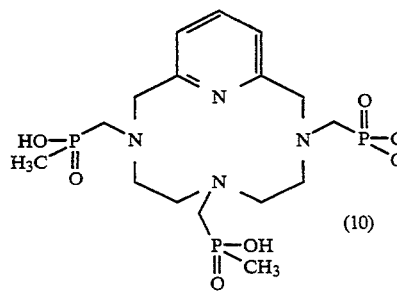
a coumpound of Formula (I)
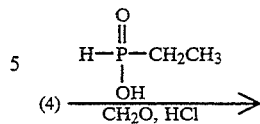
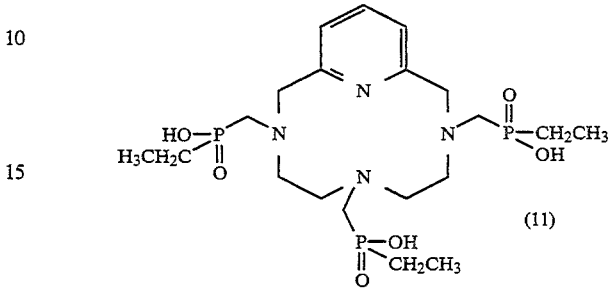
a compound of Formula (I)
Scheme 4 prepares the compounds of Formula (I) wherein X and Y=H, n=1 (but would also apply if n=2 or 3 with the corresponding change in the reagent), R has T=
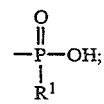
where $R^1 = -O-(C_1-C_5$ alkyl) or $C_1-C_5$ alkyl; A=-C—Br; and Q and Z=CH.

Scheme 4
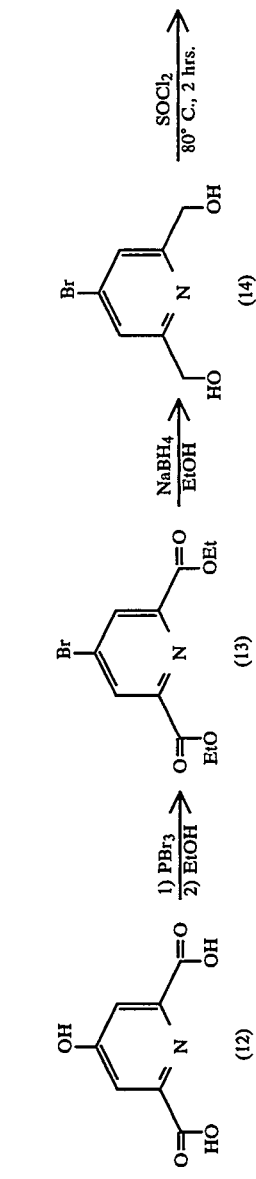
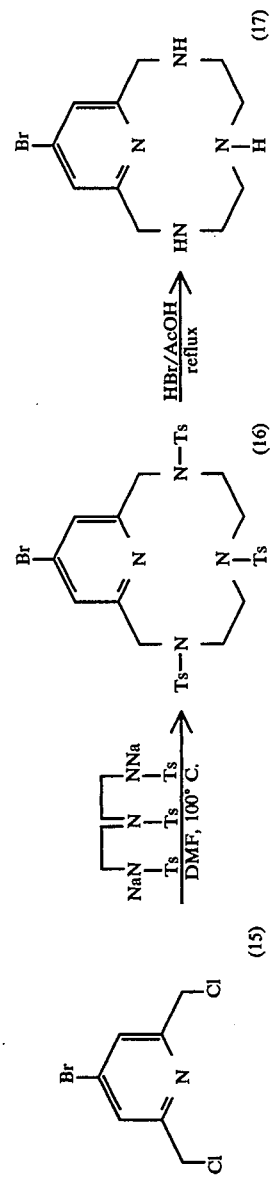

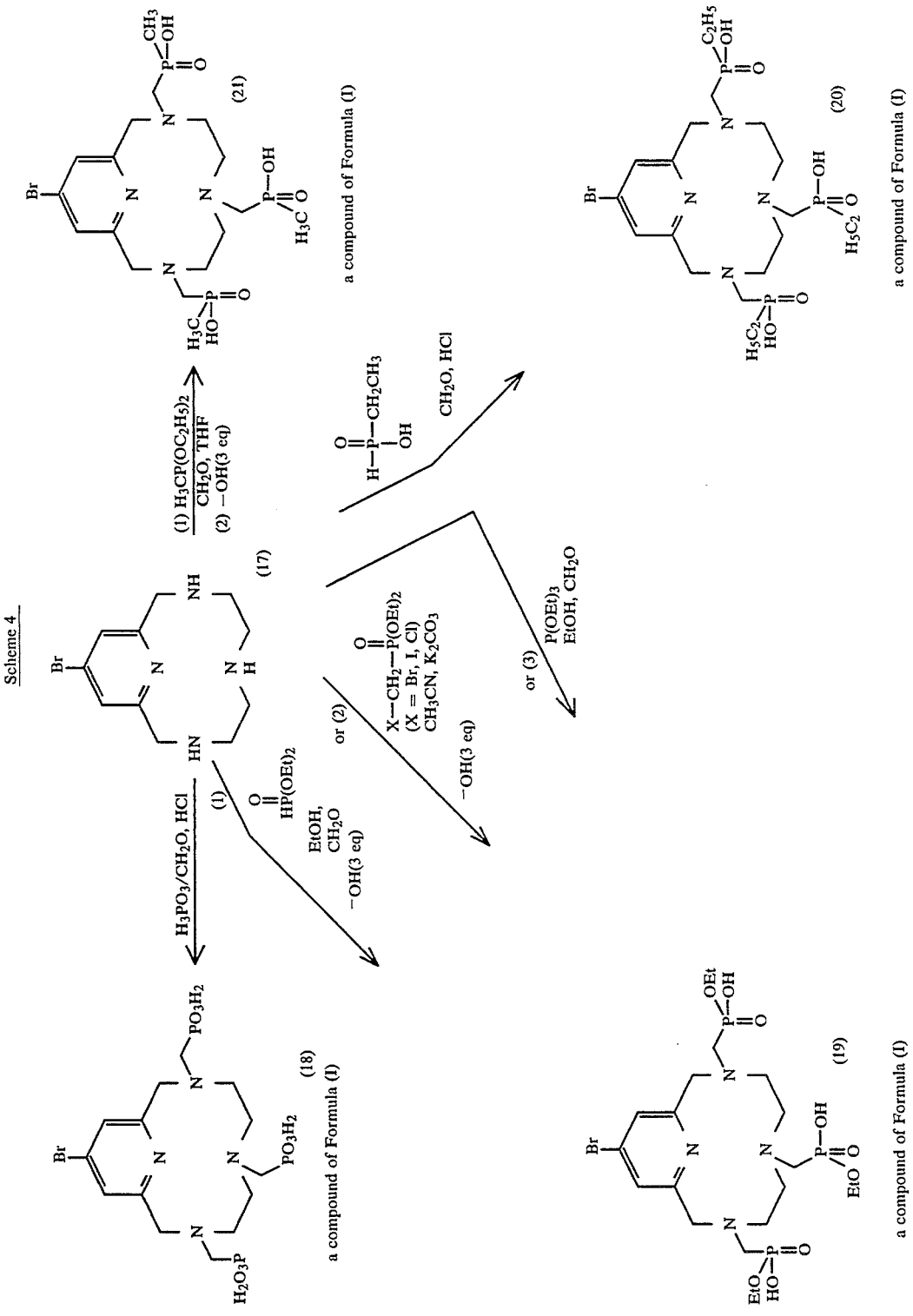

Scheme 5 prepares the compounds of Formula (I) wherein X and Y=H, n=1 (but would also apply if n=2 or 3 with the corresponding change in the reagent), R has T=
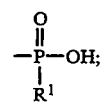
where $R^1$ =—O—($C_1$-$C_5$ alkyl) or $C_1$-$C_5$ alkyl; A=
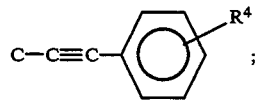
where $R^4$=H, $NO_2$, $NH_2$ or SCN; and Q and Z=CH.

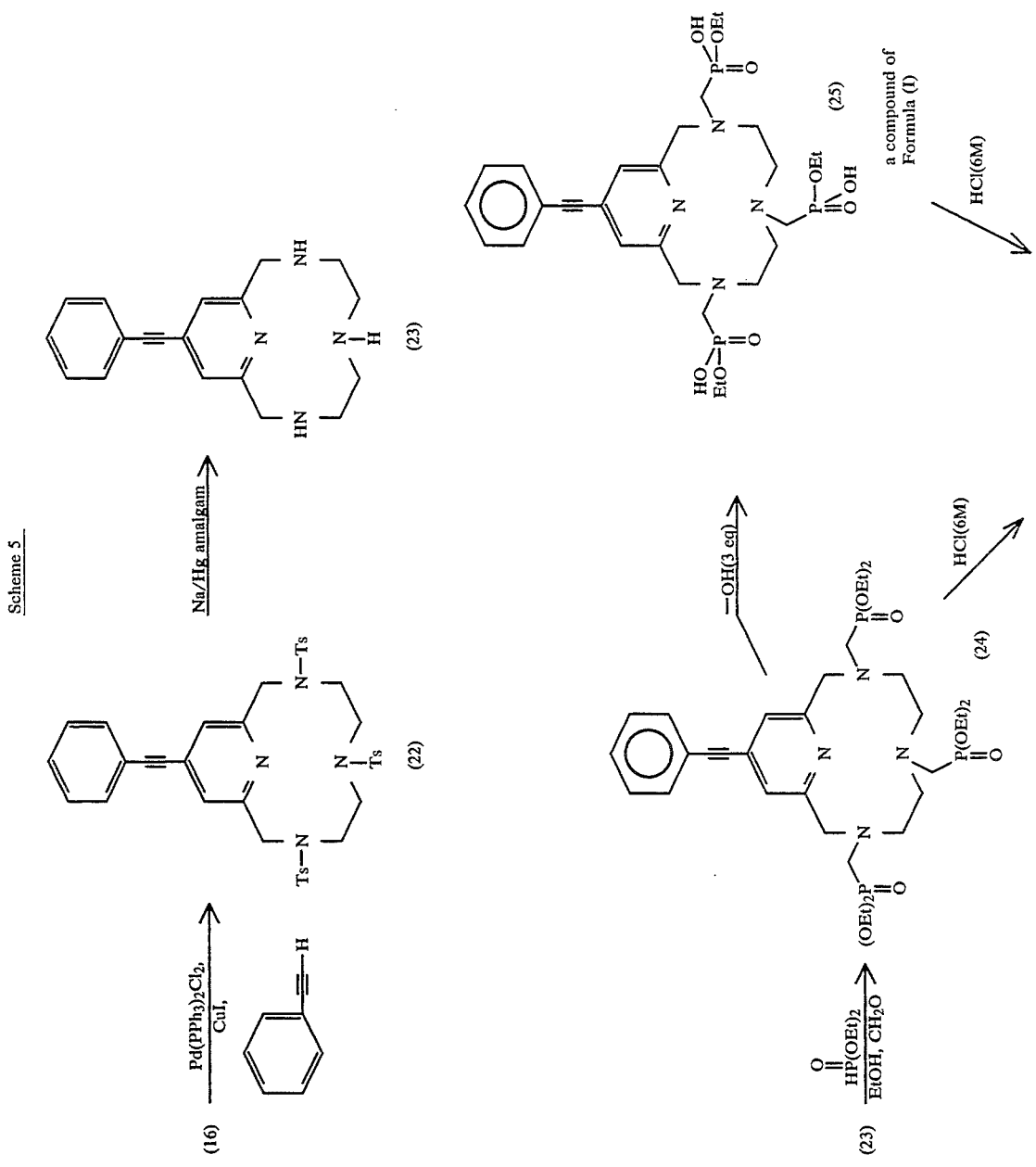

-continued
Scheme 5
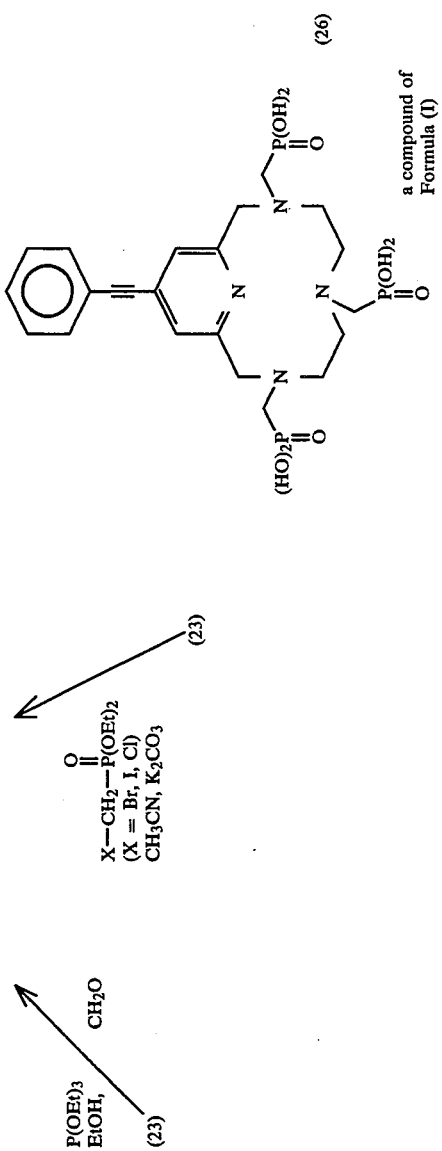

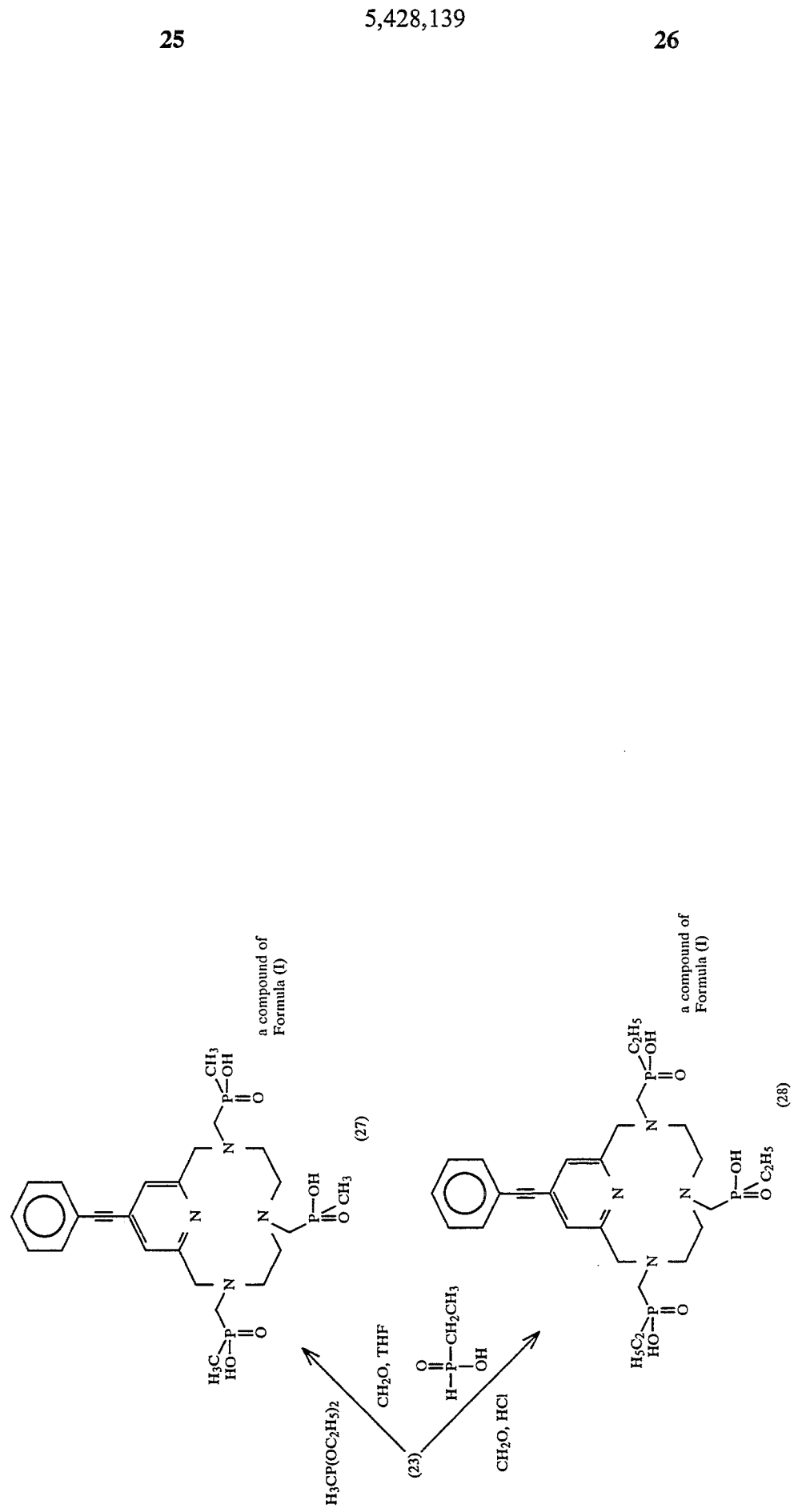

Scheme 6 prepares the compounds of Formula (I) wherein X and Y=H, n=1 (but would also apply if n=2 or 3 with the corresponding change in the reagent), R has T=
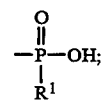
where $R^1 = -O-(C_1-C_5 \text{ alkyl})$ or $C_1-C_5$ alkyl; $A = -C-OR^8$, where $R^8 = C_1-C_5$ alkylamino; and Q and Z=CH.

Scheme 6
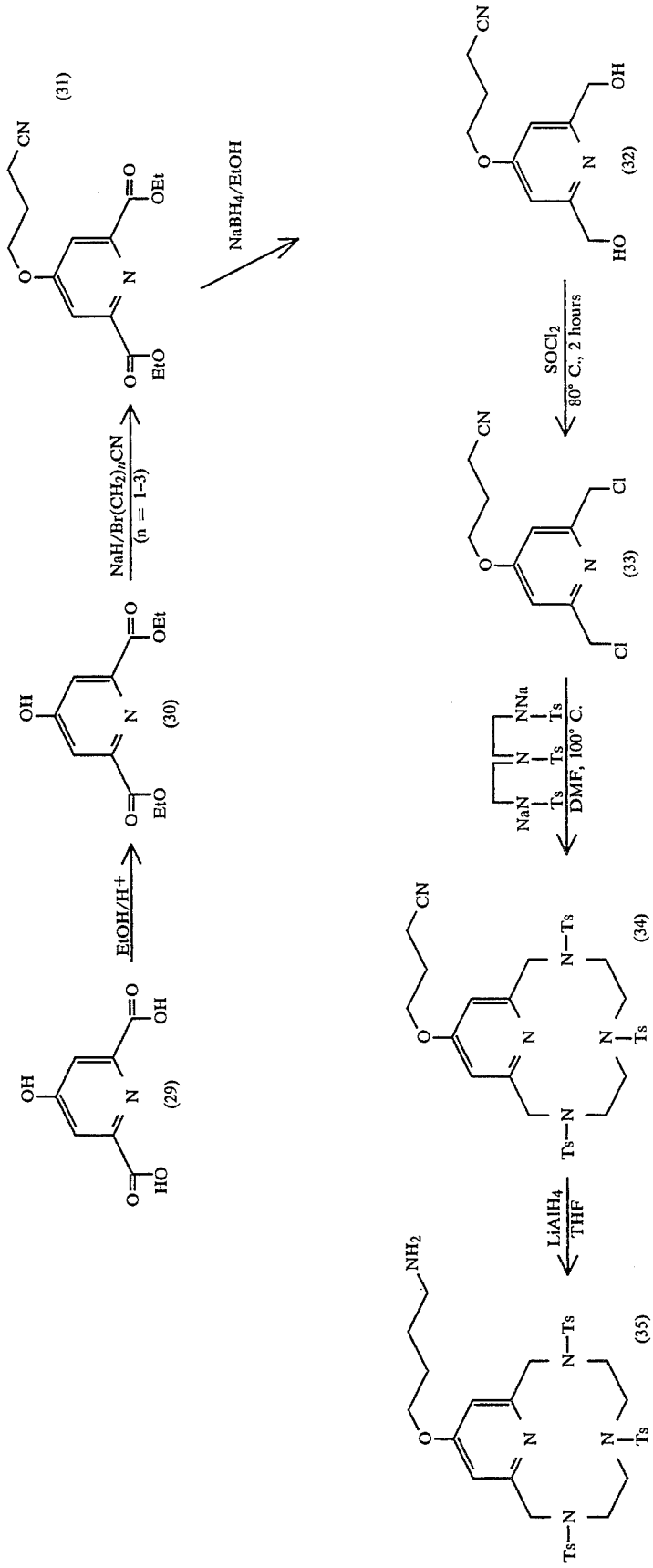

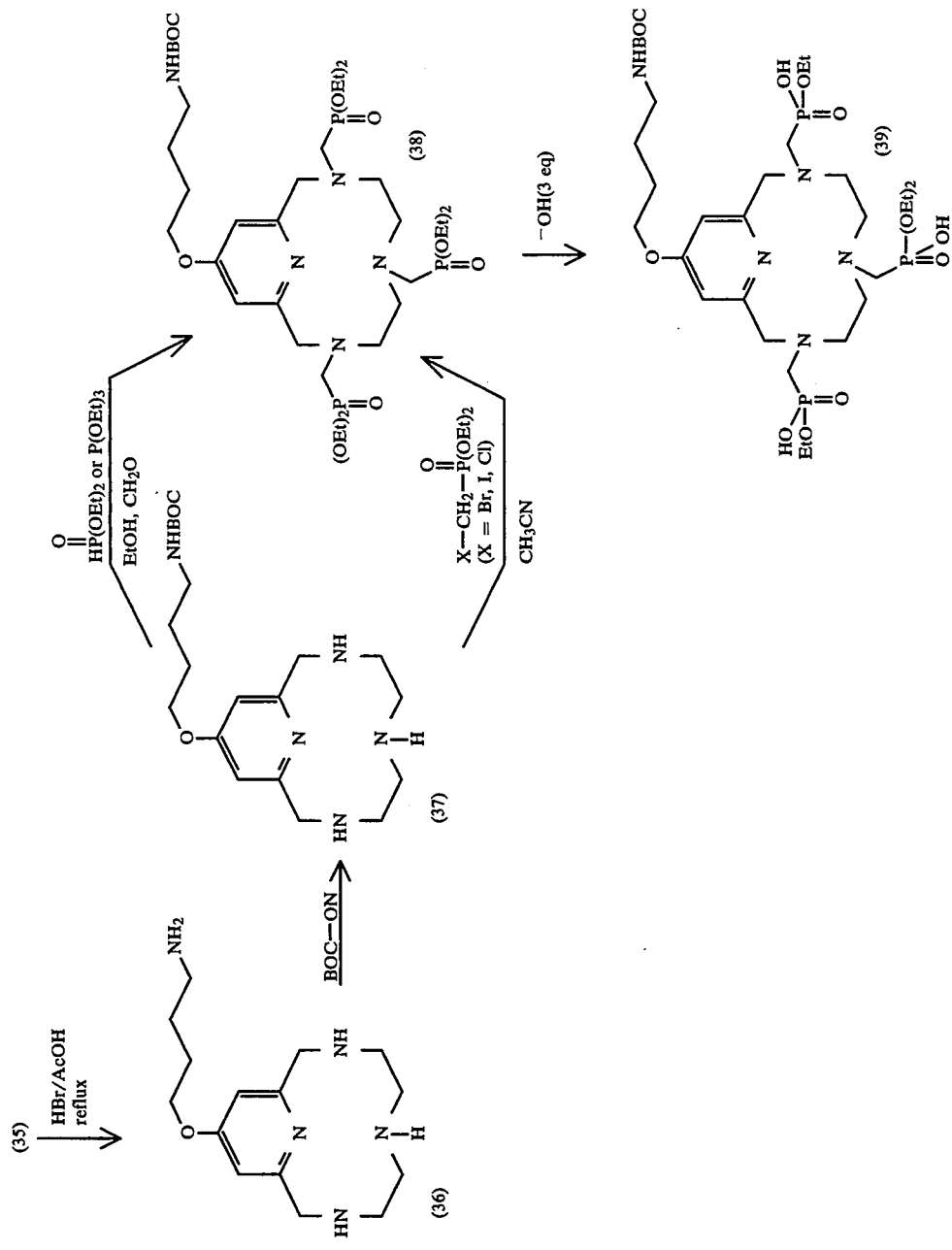

-continued
Scheme 6
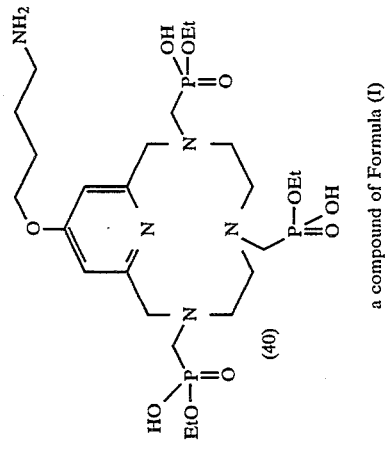
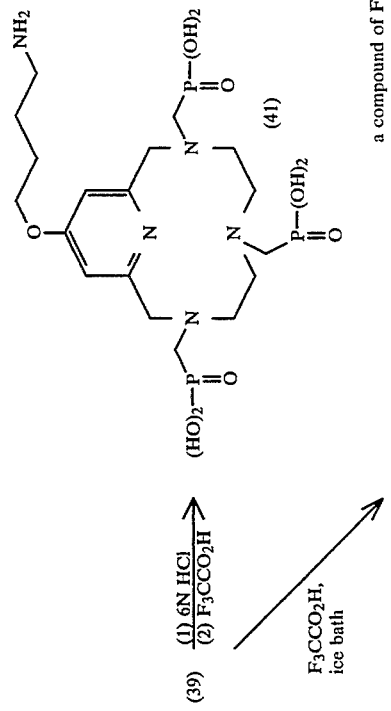

-continued
Scheme 6
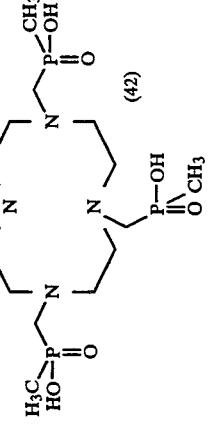

Scheme 7 prepares the compounds of Formula (I) wherein X and Y=H, n=1 (but would also apply if n=2 or 3 with the corresponding change in the reagent), R has T=
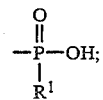
where $R^1$=—OH, —O—($C_1$-$C_5$ alkyl) or $C_1$-$C_5$ alkyl; Z=C—C(O)—$R^6$, where $R^6$=OH; and A and Q=CH.

Scheme 7
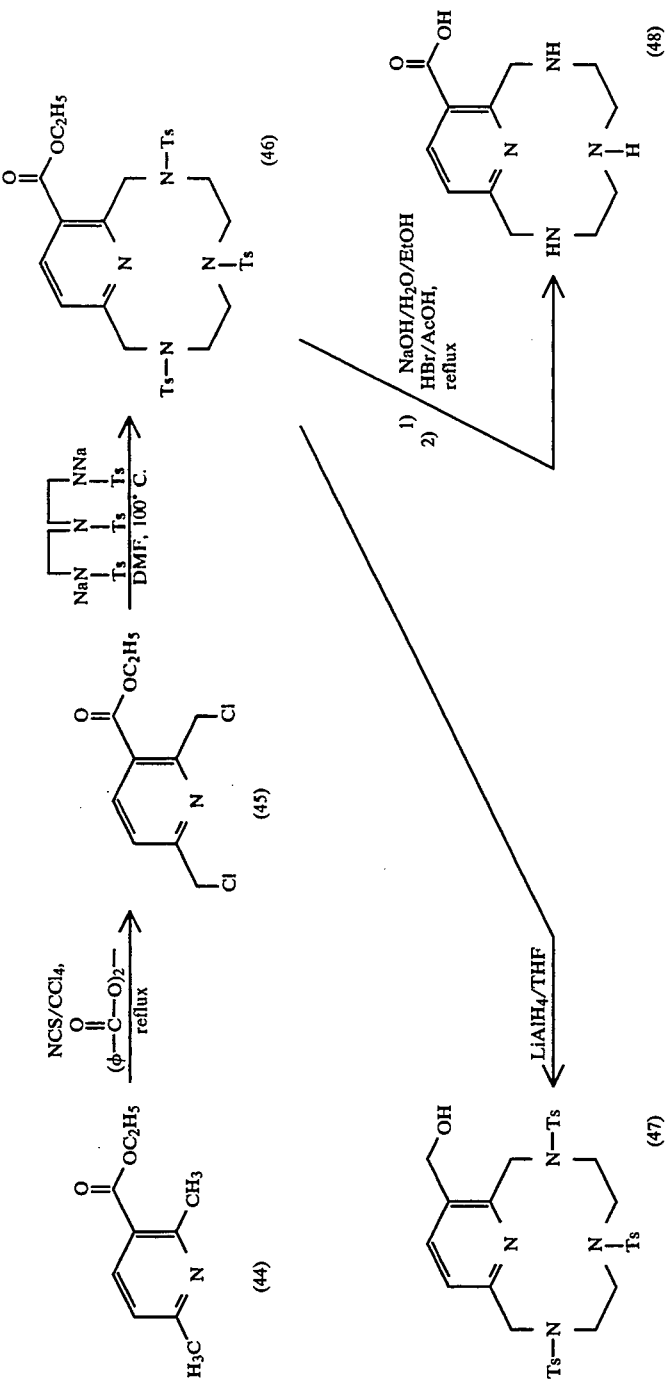
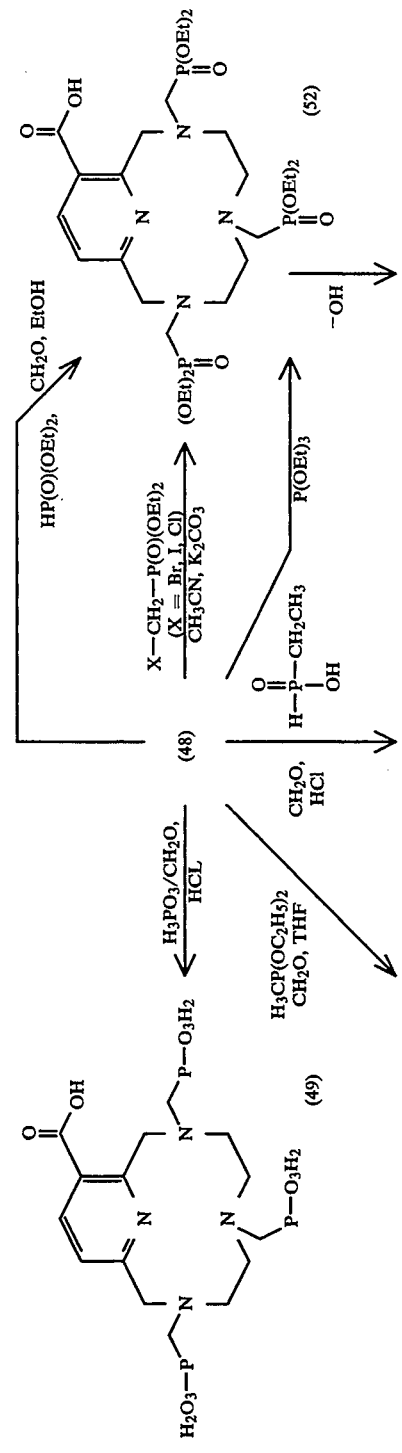

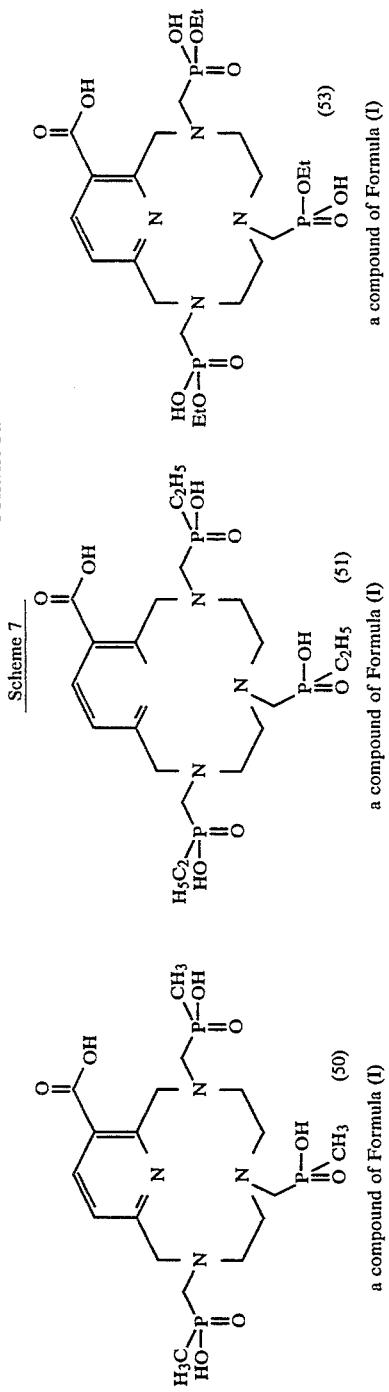

Scheme 8 prepares the compounds of Formula (I) wherein X and Y=H, n=1 (but would also apply if n=2 or 3 with the corresponding change in the reagent), R has T=
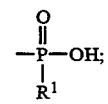
where $R^1$=—OH, —O—($C_1$-$C_5$ alkyl) or $C_1$-$C_5$ alkyl; Z=C—$CH_2$—$OR^3$, where $R^3$=benzyl; and Q and A=CH.
Scheme 8
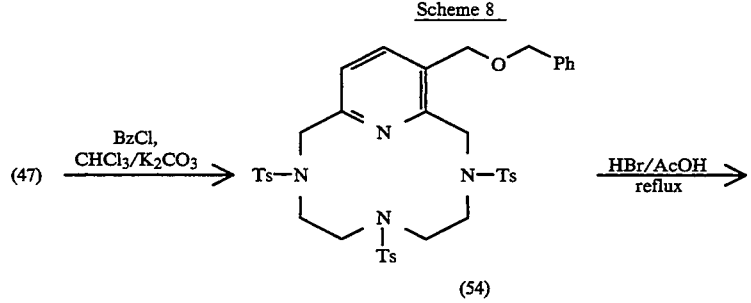
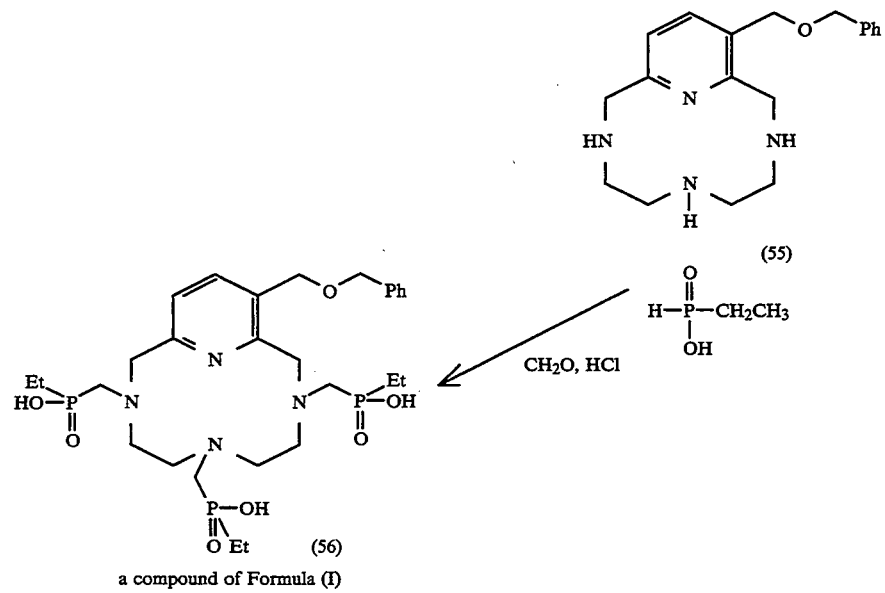
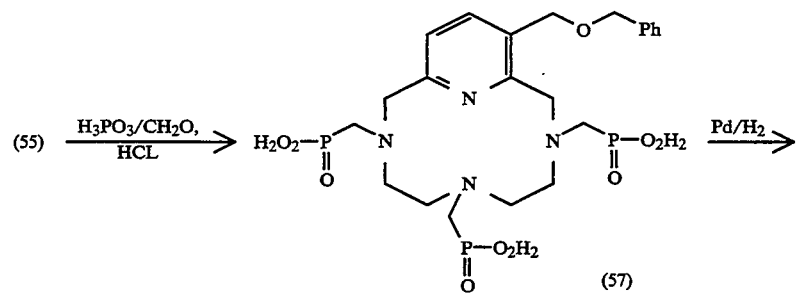

-continued
Scheme 8
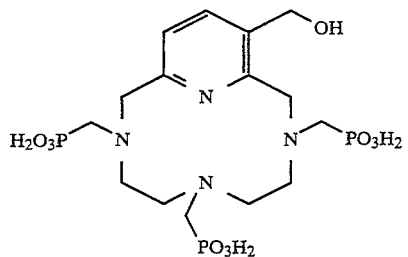
(58)
a compound of Formula (I)
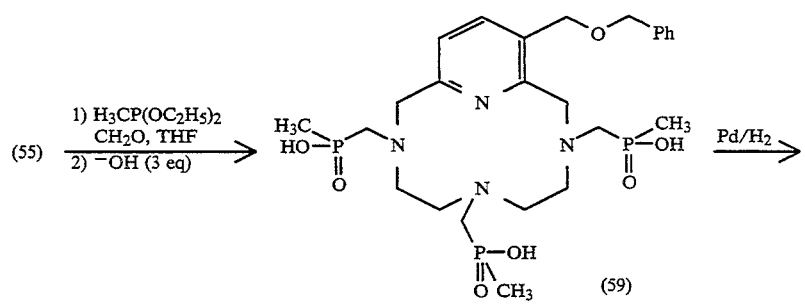
(59) a compound of Formula (I)
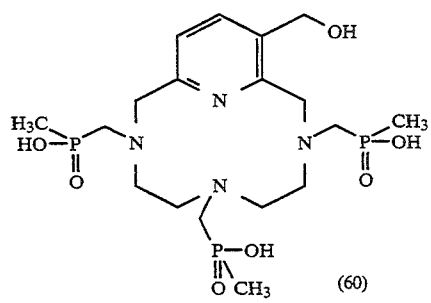
(60) a compound of Formula (I)
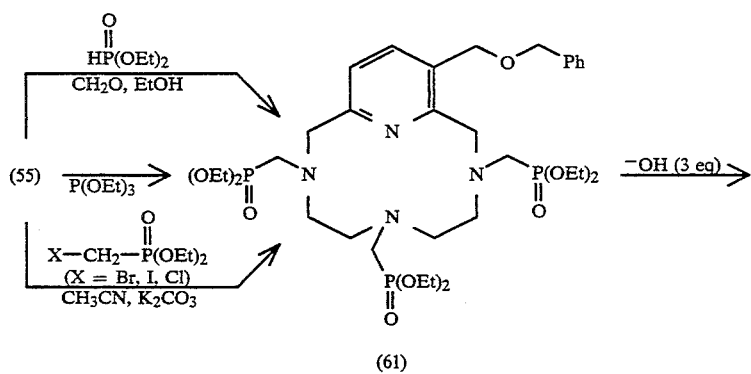
(61)

-continued
Scheme 8
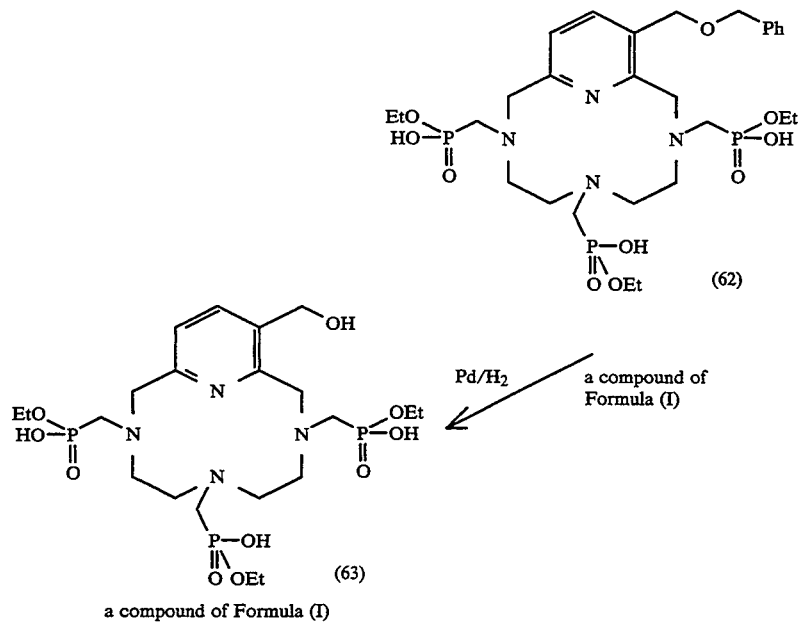
Scheme 9 prepares the compounds of Formula (I) wherein X and Y=H, n=1 (but would also apply if n=2 or 3 with the corresponding change in the reagent), R has T=
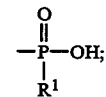
where $R^1$=—OH, —O—($C_1$–$C_5$ alkyl) or $C_1$–$C_5$ alkyl; A=N or $N^+$—$R^5$ $X^-$, where $R^5$=$C_1$–$C_{16}$ alkyl and $X^-$ is defined as before; and Q and Z=CH.
Scheme 9
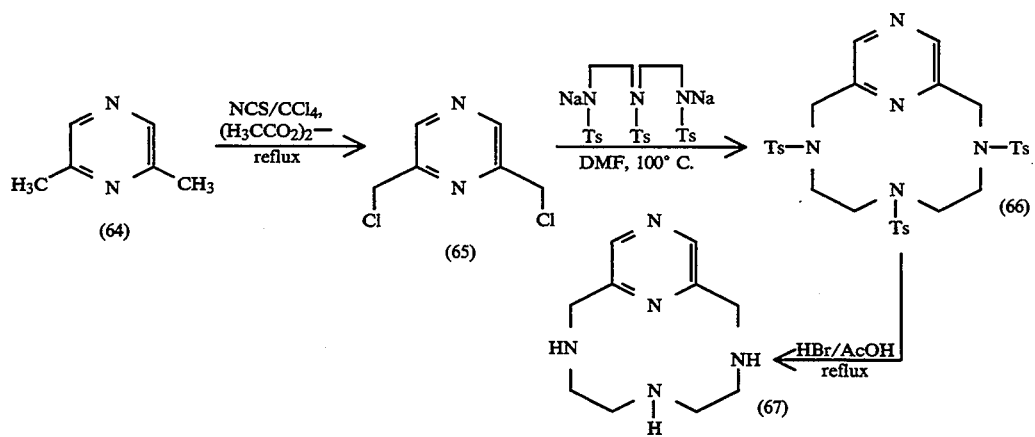

Scheme 9
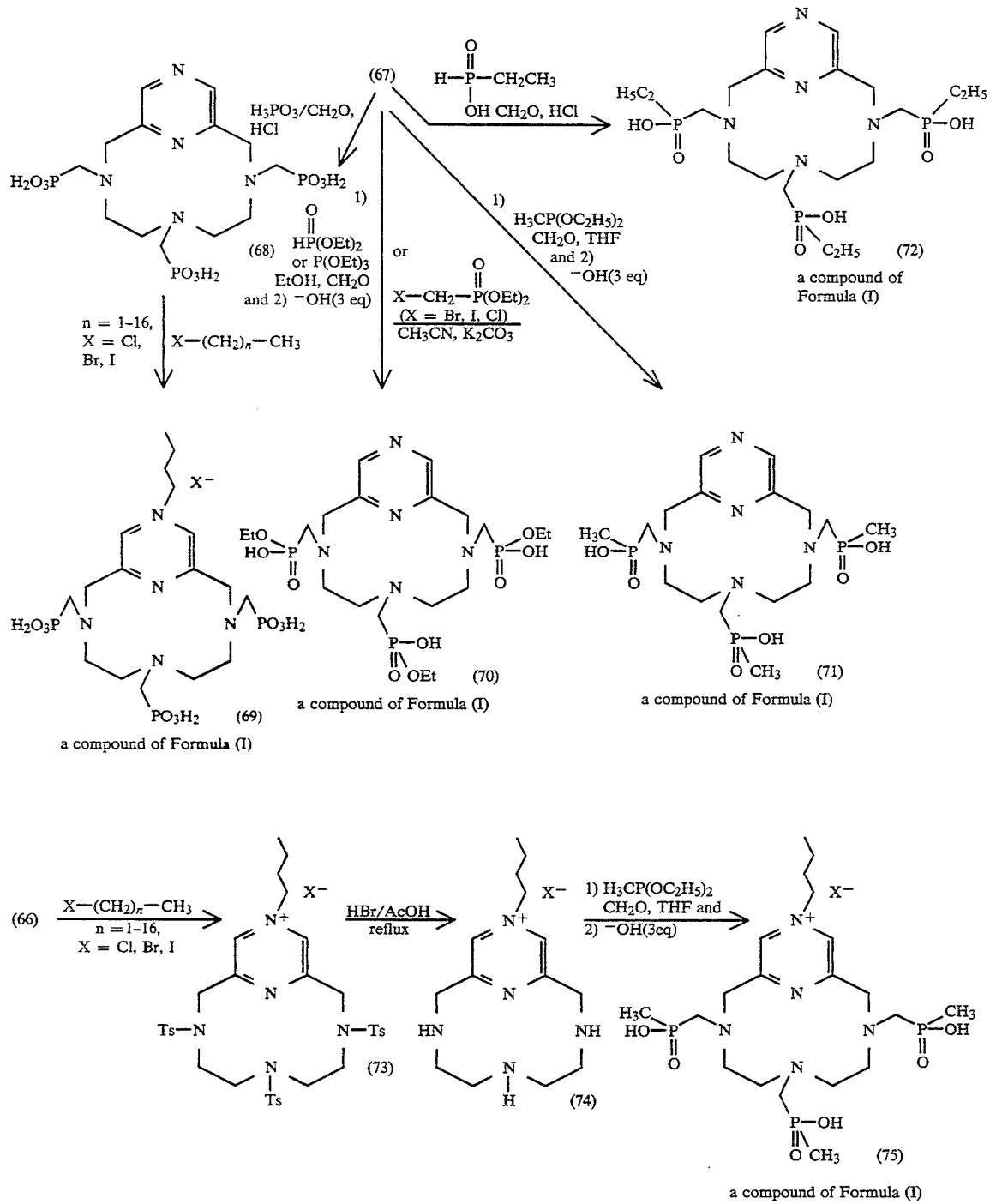
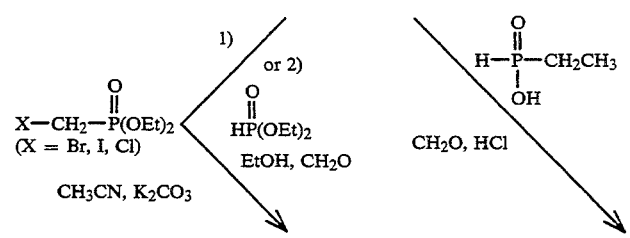

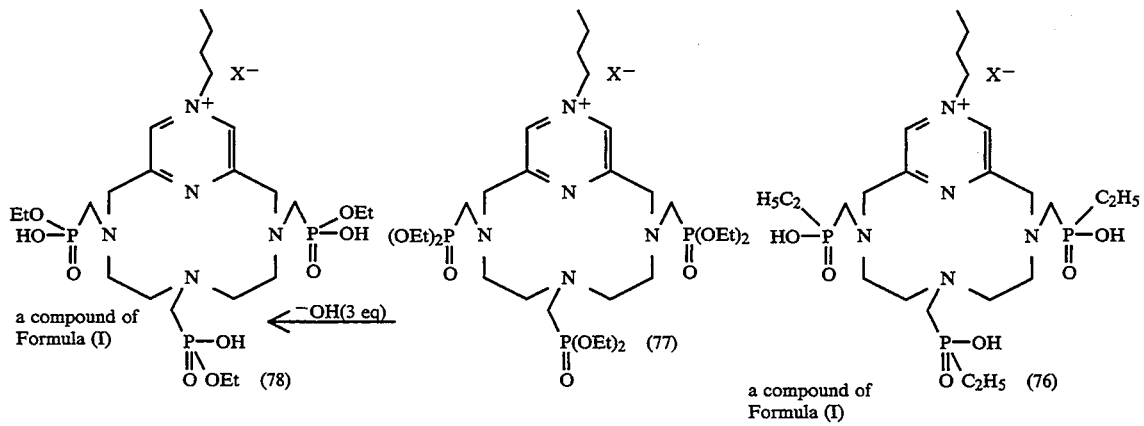
Scheme 10 prepares the compounds of Formula (I) wherein X and Y=H, n=1 (but would also apply if n=2 or 3 with the corresponding change in the reagent), R has T=
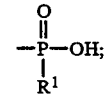
where $R^1$=—OH, —O—($C_1$-$C_5$ alkyl) or $C_1$-$C_5$ alkyl; Q=$N^+$—$R^5X^-$, where $R^5$=$C_1$-$C_{16}$ alkyl and $X^-$ is defined as before; and A and Z=CH.
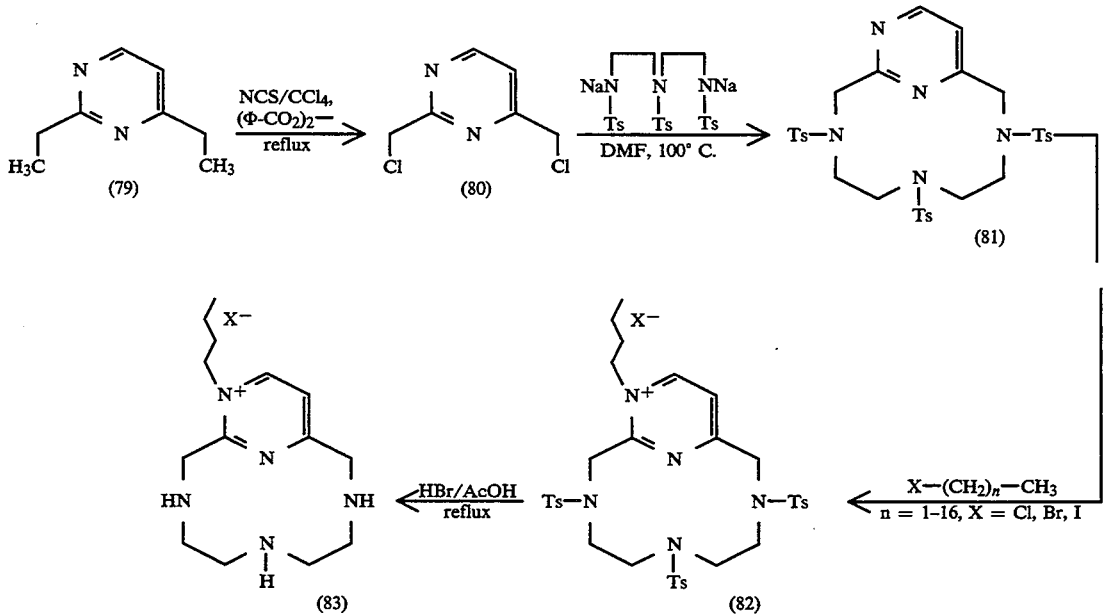

-continued
Scheme 10
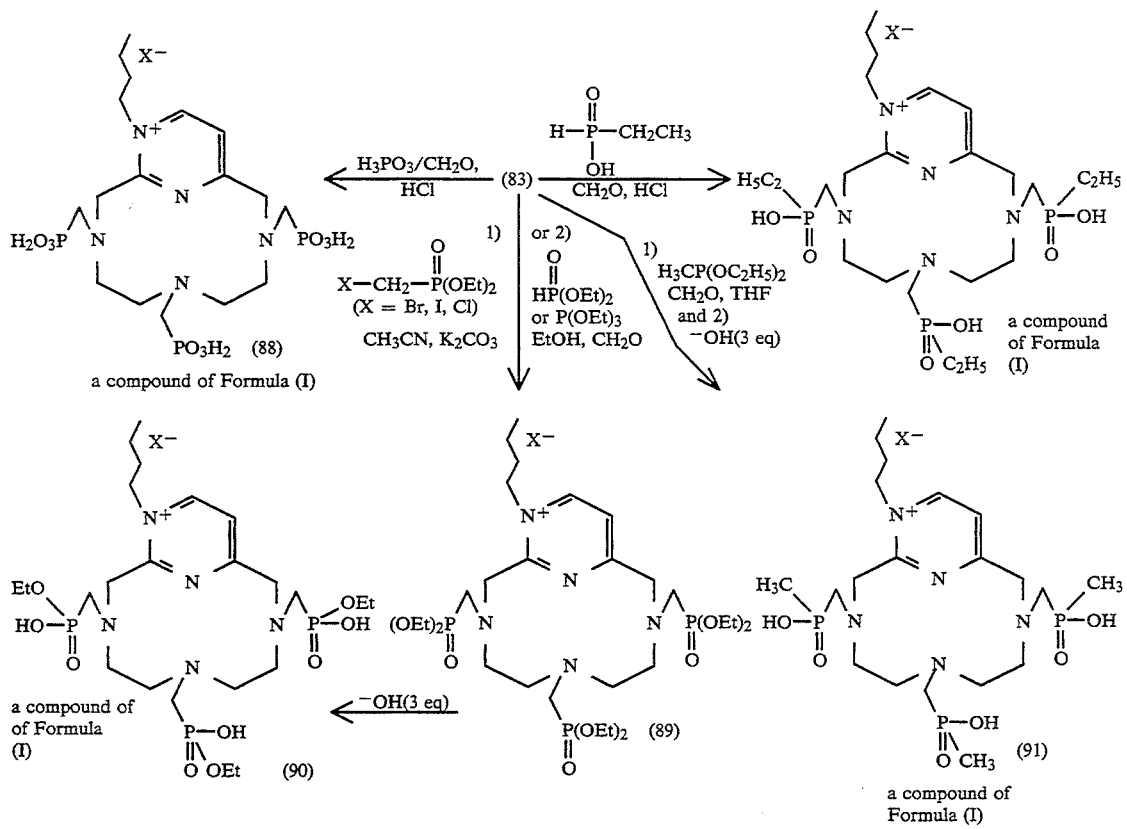
Scheme 11 prepares the compounds of Formula (I) wherein X and Y=H, n=1 (but would also apply if n=2 or 3 with the corresponding change in the reagent), R has T=
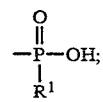
where $R^1$=—OH, —O—($C_1$-$C_5$ alkyl) or $C_1$-$C_5$ alkyl; Q=N or $N^+$—$R^5X^-$, where $R^5$=$C_1$-$C_{16}$ alkyl and $X^-$ is defined as before; and A and Z=CH.
Scheme 11
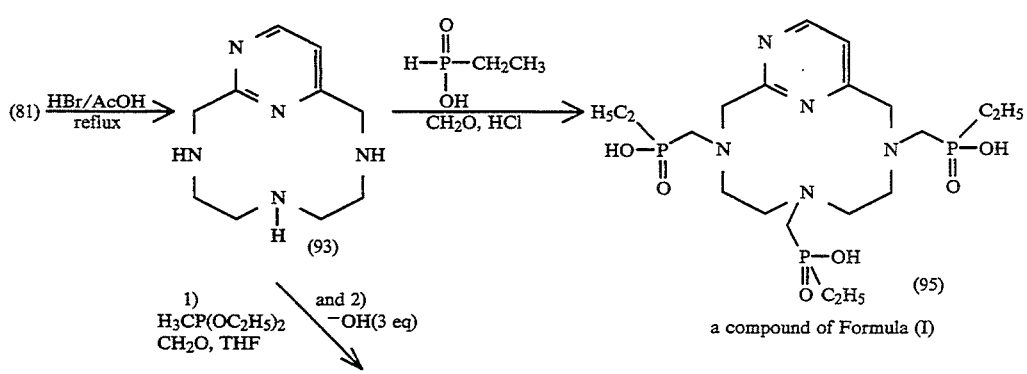

-continued
Scheme 11
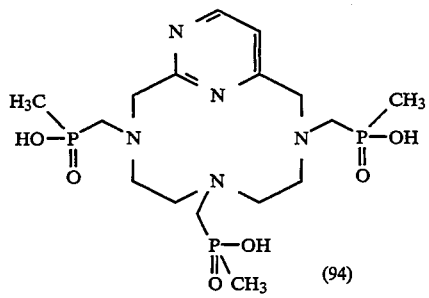
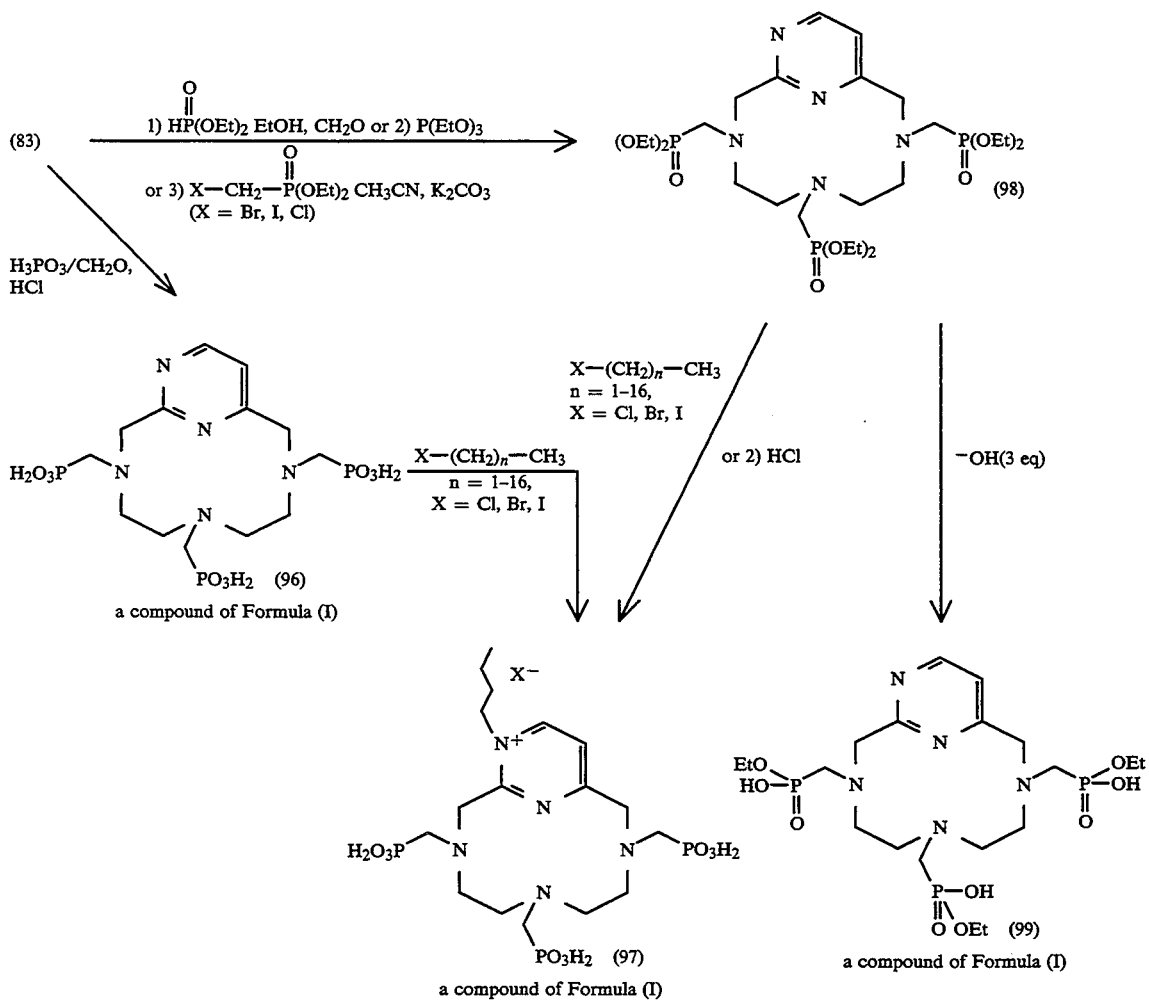
Scheme 12 prepares the compounds of Formula (I) wherein X and Y=H, n=1 (but would also apply if n=2 or 3 with the corresponding change in the reagent), R at the 3 position has T=
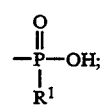
where $R^1$ = —OH or —O—($C_1$-$C_5$ alkyl); and the other R terms have T=COOH; and AQ Q and Z=CH.

Scheme 12
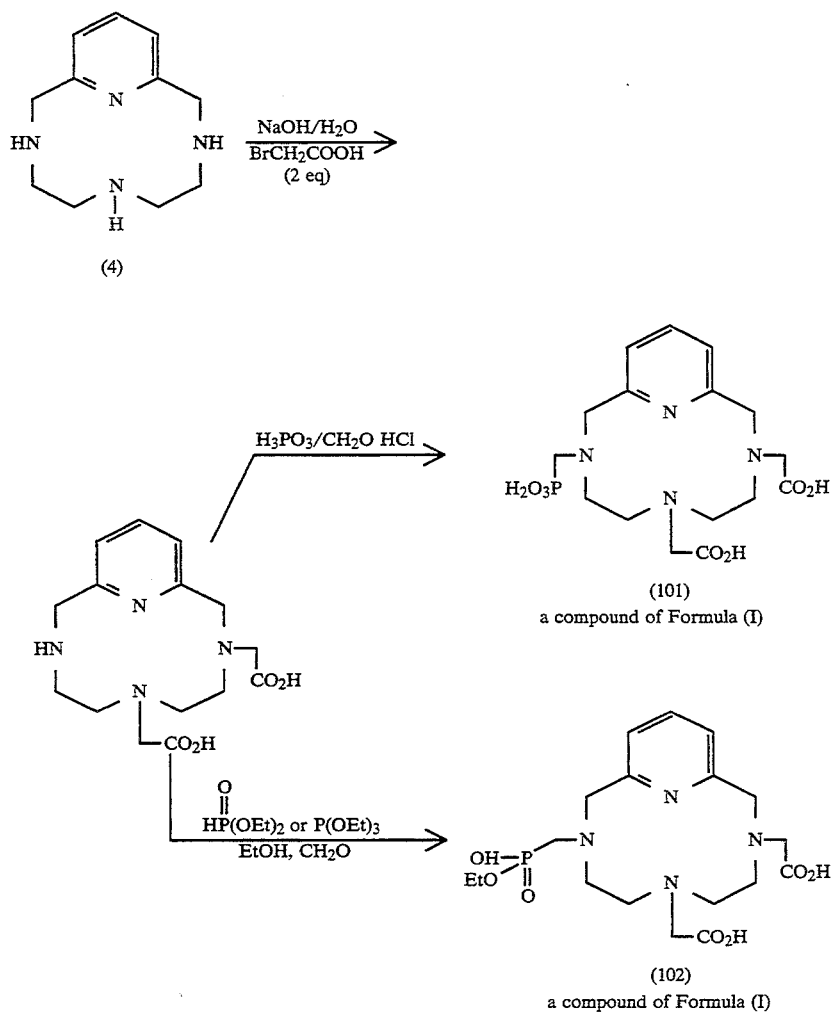
(101) a compound of Formula (I)
(102) a compound of Formula (I)
Scheme 13 prepares the compounds of Formula (I) wherein X and Y=H, n=1 (but would also apply if n=2 or 3 with the corresponding change in the reagent), R at the 3 and 6 positions have T=
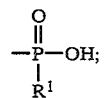
where $R^1 = $ —OH or —O—($C_1$-$C_5$ alkyl); and the R at the 9 position has T=COOH; and A Q Q and Z=CH.
Scheme 13
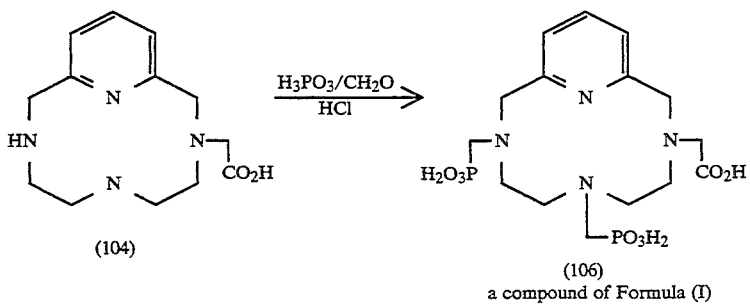
(104)
(106) a compound of Formula (I)

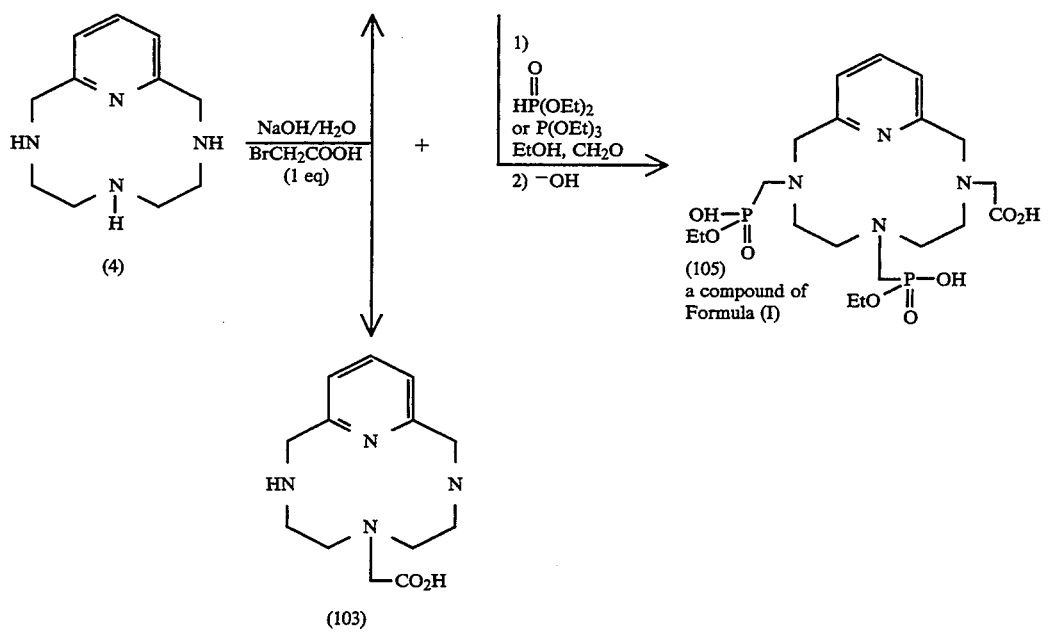

Scheme 14 prepares the compounds of Formula (I) wherein X and Y=H, n=1 (but would also apply if n=2 or 3 with the corresponding change in the reagent), R terms at the 3 and 9 positions have T=

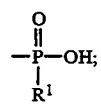

where $R^1$=—OH or —O—($C_1$-$C_5$ alkyl); and the R term at the 6 position has T=COOH; and A, Q and Z=CH.

the corresponding change in the reagent), R terms at the 3 and 9 positions have T=

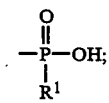

where $R^1$=—OH or —O—($C_1$-$C_5$ alkyl); and X and Y=H; the R term at the 6 position has T=

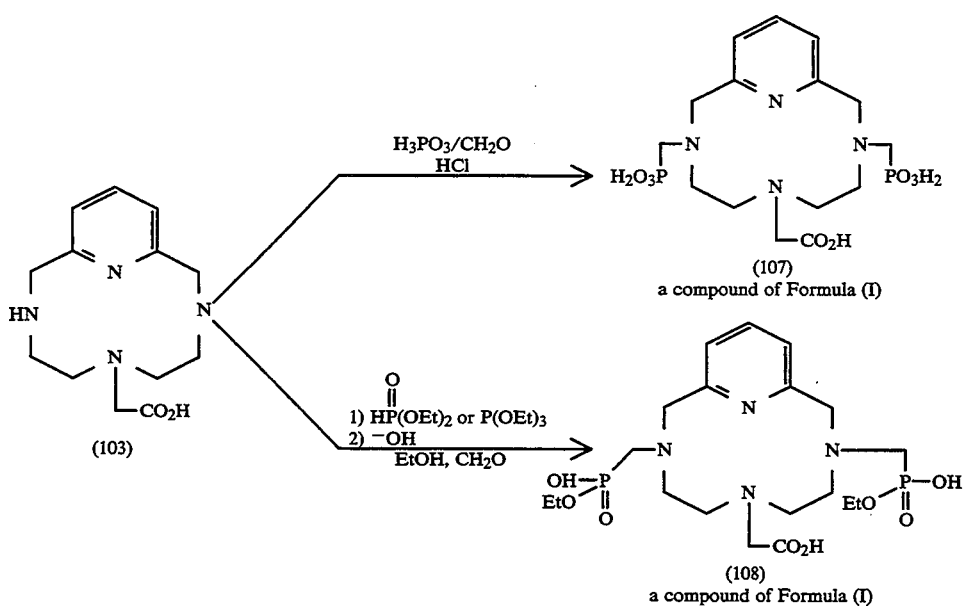

Scheme 15 prepares the compounds of Formula (I) wherein n=1 (but would also apply if n=2 or 3 with

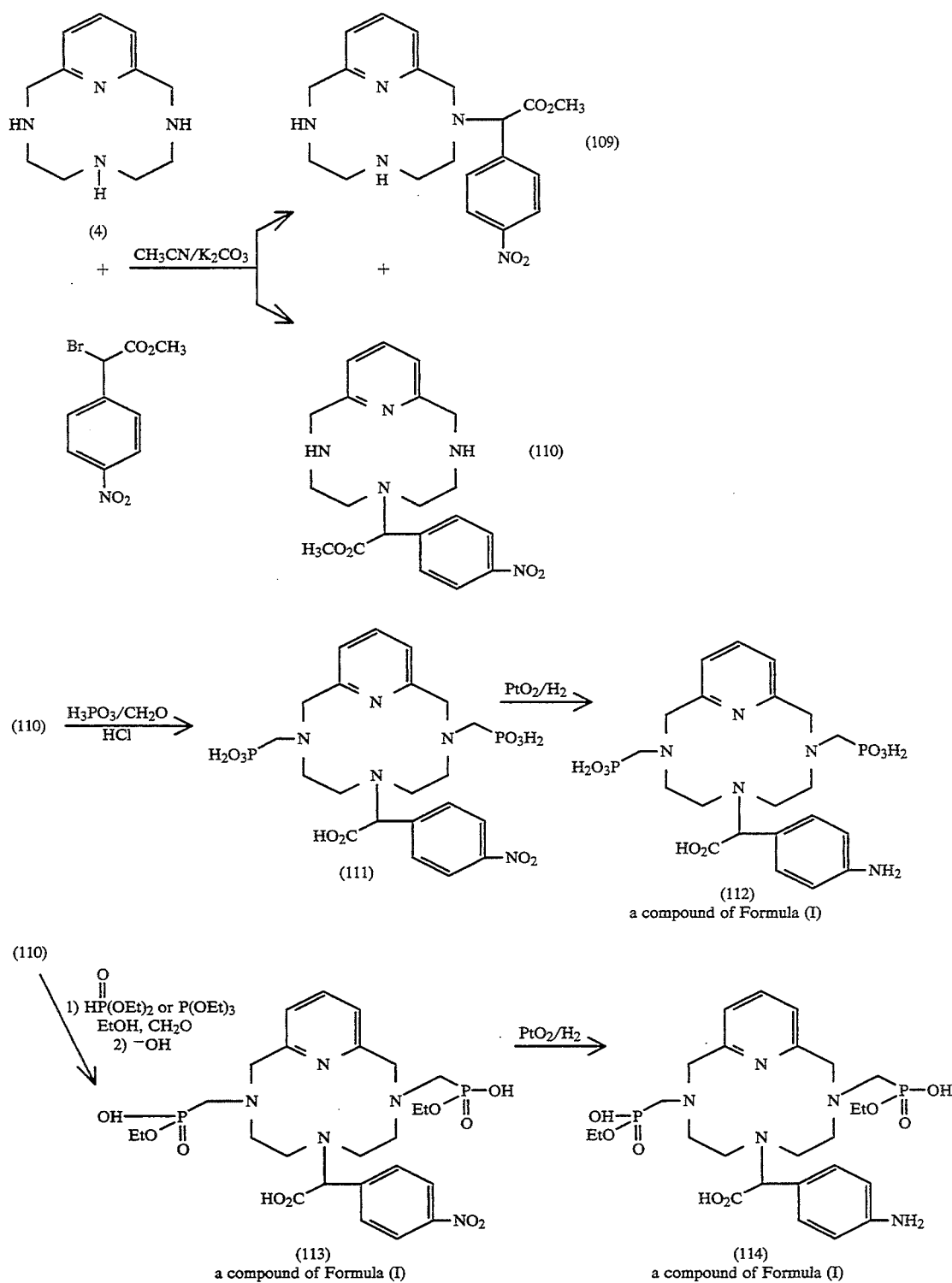
where $R^4 = NO_2$ or $NH_2$; and one of X or Y = H and the other = COOH; and A, Q and Z = CH.
Scheme 16 prepares the compounds of Formula (I) wherein n=1 (but would also apply if n=2 or 3 the corresponding change in the reagent), R terms at the 3 and 6 positions have T=

where $R^1 = $ —OH or —O—($C_1$-$C_5$ alkyl); and X and Y=H; the R term at the 9 position has T=

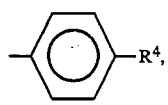

where $R^4 = NO_2$ or $NH_2$; and one of X or Y=H and the other=COOH, A, Q and Z=CH.

Scheme 16

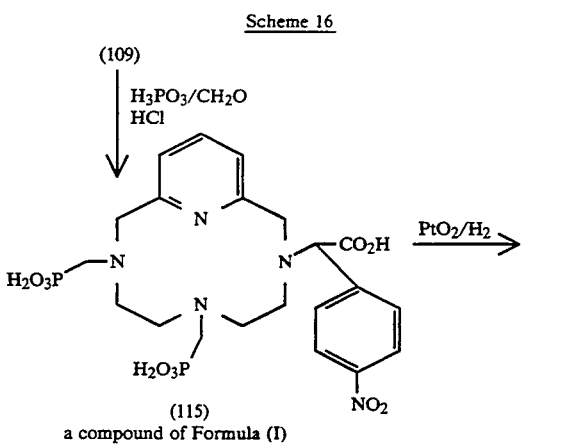

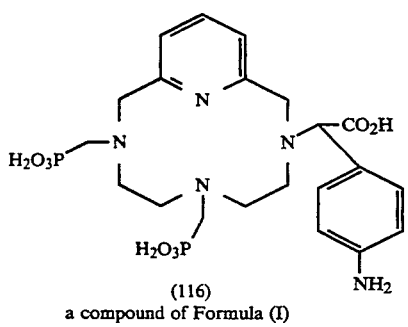

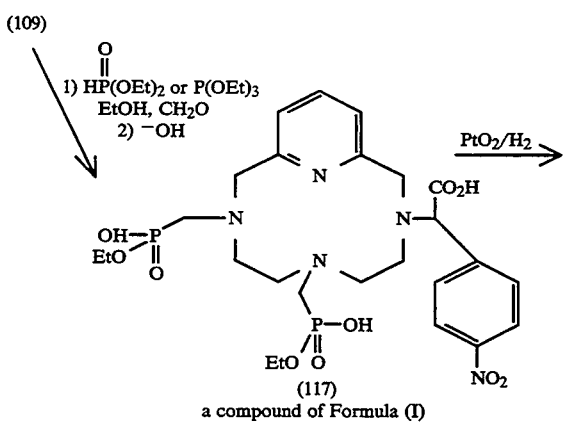

-continued
Scheme 16

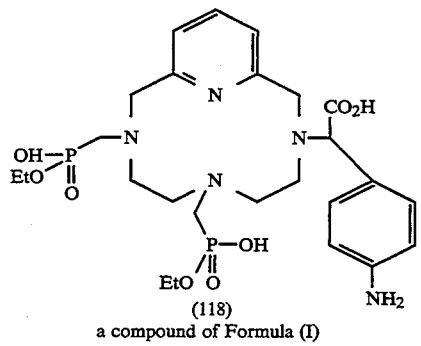

(118)
a compound of Formula (I)

In the above Schemes, the general process description illustrates specific steps that may be used to accomplish a desired reaction step. The general description of these process steps follows.

The synthetic Scheme 1 begins with a halogenation of commercially available bis-pyridyl alcohol (1) using thionyl chloride. Similar procedures for converting an alcohol to an electrophilic substrate, such as treatment with toluenesulfonyl chloride, HBr or HCl, should also result in a similarly reactive product which would work well in subsequent ring closure reactions. Macrocyclization procedures are numerous in the literature and the desired tetraazamacrocycle (3) was prepared according to the method of Stetter et al., *Tetrahedron* 37, 767–772 (1981). More general procedures have since been published which give good yields of similar macrocycles using milder conditions [A. D. Sherry et al., *J. Org. Chem.* 54, 2990-2992 (1989)]. Detosylation of the intermediate macrocycle [(3) to yield (4)] was accomplished under acidic conditions in good yield. Reductive detosylation procedures are also well known in the literature and can be adapted to the present reaction sequence. Phosphonomethylation to obtain the tris-aminophosphonic acid derivative (5; PCTMP) was conducted under typical Mannich base conditions using phosphorous acid and formaldehyde.

In addition to phosphonic acid derivatives, phosphonate esters [e.g. of formula (6prepared under organic conditions in alcohols or aprotic solvents (e.g. acetonitrile, benzene, toluene, tetrahydrofuran) and using the desired dialkylphosphite as the nucleophilic species (see Scheme 2). Depending upon the reactivity of the amine, these reactions may be conducted at a temperature between about −10° to about 100° C. In addition, trialkylphosphites can be employed under similar Mannich conditions to give the phosphonate ester via oxidation of phosphorous (III) to phosphorous (V) with simultaneous expulsion of one mole of alcohol (Arbuzov reaction). These reactions can be conducted with or without the presence of a solvent. When alcohols are employed as the solvent for either dialkyl or trialkyl phosphite reactions, it is beneficial to use the alcohol from which the corresponding phosphonate ester is derived in order to avoid alternative products arising from transesterification. Esters of this type are also prepared via N-alkylation of α-halo-dialkylphosphonates in solvents such as acetonitrile, chloroform, dimethylformamide, tetrahydrofuran or 1,4-dioxane with or without the addition of a non-nucleophilic base such as potassium carbonate at room temperature or above. The resulting perester intermediate is then readily hydrolyzed under basic conditions (aqueous hydroxide, pH=8-14, 30°-110° C.) to give the corresponding half-acid derivative.

In Scheme 3, macrocyclic methylphosphinic acids (10 and 11) are prepared under conditions similar to those described in Scheme 2. Using diethoxymethylphosphine as the nucleophilic species and paraformaldehyde, condensation can be conducted in solvents such as tetrahydrofuran, dimethylformamide, dioxane, acetonitrile or alcholic media. The resulting phosphinate ester is then hydrolyzed under acid (6N HCl, 80°-100° C.) or basic (stoichiometric quantities of base, 40°-100° C.) conditions to give the corresponding methylphosphonic acid. Alternatively, the method devised by A. D. Sherry et al. (*Inorg. Chem.*, submitted 1991) using ethylphosphonic acid generated in situ can be used to obtain phosphinate derivatives having increased lipophilic character.

Scheme 4 illustrates an approach to incorporate additional functionality into the pyridine unit of the 12-membered tetraazamacrocycle. Thus, chelidamic acid (Sigma Chemical Company; 12) can be converted to the bis-halomethyl derivative (13) having appropriate substitution at the pyridyl 4-position. Transformations leading to this intermediate are general in nature and its preparation is described by Takalo et al. [*Acta Chemica Scandinavica* B 42, 373-377 (1988)]. Subsequent macrocyclization using this intermediate (15) can be accomplished by the standard DMF reaction at 100° C. with the soliotritosylated triamine, or at room temperature with the tritosylated free base and potassium carbonate, sodium carbonate, or cesium carbonate as base to give products similar to those previously described. Subsequent reactions leading to phosphonate half-acids and phosphinate functionality are identical to those transformations and conditions described in the preceding Schemes.

In Scheme 4, 4-halopyridyl substituted macrocycles (16) are described which can undergo substitution at the 4-position of the pyridyl moiety as described in Scheme 5. Thus, organometallic Pd(II) complexes can be employed to facilitate the coupling reaction between phenylacetylene and phenylacetylene derivatives and the pyridyl macrocycle. Typical reaction conditions for this transformation utilize anhydrous conditions with triethylamine as solvent and at reaction temperature between about 10° to about 30° C. for optimum yields. The identical product can also be obtained using Cu(I) phenylacetylide in anhydrous pyridine at a temperature between about 80° to about 110° C. In addition, standard anionic alkylation procedures can be employed to affect substitution on the pyridine nucleus with, for example, sodioalkoxides in DMF or dioxane at from about 80° to about 100° C. using bases such as potassium carbonate or sodium hydroxide. Macrocyclic tetraazamacrocycles (24, 25, 26, 27, 28) derivatized in this manner are compatible with transformations described in previous Schemes resulting in analogous phosphonate chelants.

A variation of 4-pyridyl substitution is described in Scheme 6 whereby the 4-hydroxypyridyl moiety (29) is alkylated with a bromoalkylnitrile yielding an intermediate ether linked nitrile (31) which is subsequently incorporated into the macrocyclic structure. This type of alkylation procedure is best accomplished under anhydrous conditions in an aprotic solvent such as tetrahydrofuran (THF) and using a non-nucleophilic base such as sodium hydride or butyllithium at temperatures between from about −30° to about 80° C. The generality of this approach has been described by Chaubet et al., for acyclic analogs [*Tetrahedron Letters* 31 (40), 5729-5732 (1990)]. The macrocyclic nitrile prepared in this manner can be reduced to the primary amine (36) by standard procedures followed by protection of the primary amine with 2-(t-butoxycarbonyloxyimino)-2-phenylacetonitrile (BOC-ON; 37). Subsequent functionalization of the macrocyclic secondary amines (38, 39, 40, 41, 42, 43) can then be accomplished by the procedures discussed with the additional requirement that the BOC protecting group be removed using trifluoroacetic acid as described in Scheme 6.

Functionalization can also be carried out on the 3-position of the pyridine ring within the macrocyclic structure as illustrated in Scheme 7. Newkome et al. [*Tetrahedron* 39(12), 2001-2008 (1983)] has previously described the synthesis of ethyl 2,6-halomethylnicotinate (45) which serves as the initial starting material in this synthetic route. Thus, the tris-tosylated macrocycle intermediate (46) can be detosylated under acidic conditions (HBr/AcOH, 25°-115° C.) with simultaneous hydrolysis to yield the nicotinic acid derivative (48), or reduction of the ester in refluxing ethanol prior to detosylation will result in the 3-hydroxymethyl intermediate (47). The nicotinic acid macrocycle can then be substituted into the general scheme for secondary amine functionalization to yield the various types of phosphonate chelants of Formula (I) (49, 50, 51, 52, 53).

In contrast, the 3-hydroxymethyl analog is advantageously protected prior to functionalization of the macrocyclic amines. The benzyl (Bz) protecting group is shown in Scheme 8 since it must be resistant to the severe acid conditions encountered in the detosylation step. After appropriate functionalization of the secondary amines has been accomplished as described in previous Schemes, the benzyl group is removed under mild catalytic hydrogenation conditions (58).

Macrocyclic derivatives can also be prepared as in Schemes 12-14 where both carboxylate and phosphonate chelating functionalities are present in the same molecule. Thus, varying degrees of carboxylate functionality can be introduced under typical aqueous alkylation procedures using bromoacetic acid. Following this step, the remaining amines can be phosphonomethylated by procedures discussed in previous Schemes using formaldehyde and phosphorous acid, dialkyl phosphonates or trialkyl phosphites.

Schemes 15 and 16 delineate a synthetic approach which introduces an aromatic nitrobenzyl substituent at one of the macrocyclic nitrogen positions. Typically, the macrocyclic amine is mono-N-functionalized in an organic solvent such as acetonitrile or DMF at room temperature using a non-nucleophilic base such as potassium carbonate. Additional functionalization of the remaining nitrogen positions is then preformed by methods and conditions described in previous Schemes. After the introduction of the desired chelating moieties, the nitro group is reduced using platinum oxide and hydrogen in water. In this form, the chelating agent is compatible with conjugation techniques which will enable attachment to larger synthetic or natural molecules.

The metal ions used to form the complexes of this invention are $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{99m}$Tc, $^{67}$Ga, $^{68}$Ga, $^{105}$Rh, $^{97}$Ru, $^{111}$In, $^{113m}$In or $^{115m}$In. The anion present is halide, preferably chloride, or salt free (metal oxide).

The complexes are prepared by methods well known in the art. Thus, for example, see Chelating Agents and Metal Chelates, Dwyer & Mellor, Academic Press (1964), Chapter 7. See also methods for making amino acids in Synthetic Production and Utilization of Amino Acids, (edited by Kameko, et al.) John Wiley & Sons (1974). An example of the preparation of a complex involves reacting a bicyclopolyazamacrocyclophosphonic acid with the metal ion under aqueous conditions at a pH from 5 to 7. The complex formed is by a chemical bond and results in a stable radionuclide composition, e.g. stable to the disassociation of the radionuclide from the ligand.

The complexes of the present invention are administered at a ligand to metal molar ratio of at least about 1:1, preferably from 1:1 to 3:1, more preferably from 1:1 to 1.5:1. A large excess of ligand is undesirable since uncomplexed ligand may be toxic to the animal or may result in cardiac arrest or hypocalcemic convulsions.

The antibodies or antibody fragments which may be used in the conjugates described herein can be prepared by techniques well known in the art. Highly specific monoclonal antibodies can be produced by hybridization techniques well known in the art, see for example, Kohler and Milstein [Nature, 256, 495-497 (1975); and Eur. J. Immunol., 6, 511-519 (1976)]. Such antibodies normally have a highly specific reactivity. In the antibody targeted conjugates, antibodies directed against any desired antigen or hapten may be used. Preferably the antibodies which are used in the conjugates are monoclonal antibodies, or fragments thereof having high specificity for a desired epitope(s). Antibodies used in the present invention may be directed against, for example, tumors, bacteria, fungi, viruses, parasites, mycoplasma, differentiation and other cell membrane antigens, pathogen surface antigens, toxins, enzymes, allergens, drugs and any biologically active molecules. Some examples of antibodies or antibody fragments are 1116-NS-19-9, 1116-NS-3d, 703D4, 704A1 and B72.3. All of these antibodies have been deposited in ATCC. A more complete list of antigens can be found in U.S. Pat. No. 4,193,983, which is incorporated herein by reference. The conjugates of the present invention are particularly preferred for the diagnosis of various cancers.

This invention is used with a physiologically acceptable carrier, excipient or vehicle thereof. The methods for preparing such formulations are well known. The formulations may be in the form of a suspension, injectable solution or other suitable formulations. Physiologically acceptable suspending media, with or without adjuvants, may be used.

An "effective amount" of the formulation is used for diagnosis and therapy. The dose will vary depending on the disease and physical parameters of the animal, such as weight. In vivo diagnostics are also contemplated using formulations of this invention.

The invention will be further clarified by a consideration of the following examples, which are intended to be purely exemplary of the present invention.

Some terms used in the following examples are defined as follows:

LC=liquid chromatography, purifications were carrier out at low pressure using Dionex 2010i system fitted with a hand-packed Q-Sepharose ™ anion exchange column (23×2 cm).
DMF=dimethylformamide.
AcOH=acetic acid.
ICP=inductively coupled plasma.
g=gram(s).
mg=milligrams.
kg=kilogram(s).
mL=milliliter(s).
$\mu$L=microliter(s).

pH Stability General Procedure

A stock $^{153}$SmCl$_3$ solution was prepared by adding 2 $\mu$L of 3×10$^{-4}$M $^{153}$SmCl$_3$ in 0.1N HCl to 2 mL of a 3×10$^{-4}$M SmCl$_3$ carrier solution. Appropriate ligand solutions were then prepared in deionized water. The 1:1 ligand/metal complexes were then prepared by combining the ligands (dissolved in 100-500 $\mu$L of deionized water) with 2 mL of the stock $^{153}$SmCl$_3$ solution, followed by through mixing to give an acidic solution (pH=2). The pH of the solution was then raised to 7.0 using 0.1N NaOH. The percent metal as a complex was then determined by passing a sample of the complex solution through a Sephadex ™ G-50 column, eluting with 4:1 saline (85% NaCl/NH$_4$OH) and collecting 2×3 mL fractions. The amount of radioactivity in the combined elutions was then compared with that left on the resin (non-complexed metal is retained on the resin). The pH stability profile was generated by adjusting the pH of an aliquot of the complex solution using 1M NaOH or 1M HCl and determining the percent of the metal existing as a complex using the ion exchange method described above.

STARTING MATERIALS

Example A

Preparation of 2,6-bis(chloromethyl)pyridine.

To 100 mL of thionyl chloride that was cooled (ice bath) was added 24 g (0.17 mol) of 2,6-bis(hydroxymethyl)pyridine. After 30 min, the reaction mixture was warmed to room temperature, then refluxed for 1.5 hrs. After cooling the reaction mixture to room temperature, the solid which formed was filtered, washed with benzene and dried in vacuo. The solid was then neutralized with saturated NaHCO$_3$, filtered and dried to yield 23.1 g (71.5%) of the titled product as an off-white crystalline solid, mp 74.5°-75.5° C., and further characterized by:

$^1$H NMR (CDCl$_3$) $\delta$4.88 (s, 4H), 7.25-7.95 (m, 3H).

Example B

Preparation of 3,6,9-tris(p-tolylsulfonyl)-3,6,9,15-tetraazabicyclo[9.3.1]pentadeca-1(15),11,13-triene.

A DMF solution (92 mL) of 6.9 g (11.4 mmol) of 1,4,7-tris(p-tolylsulfonyl)diethylenetriamine disodium salt was stirred and heated to 100° C. under nitrogen. To the solution was added dropwise over 45 min 2 g (11.4 mmol) of 2,6-bis(chloromethyl)pyridine (prepared by the procedure of Example A) in 37 mL of DMF. When the addition was completed the reaction mixture was stirred at 40° C. for 12 hrs. To the reaction mixture was then added 50-75 mL of water, resulting in immediate dissolution of NaCl, followed by precipitation of the title product. The resulting slurry was then filtered and the solid washed with water and dried in vacuo. The title product was obtained as a light-tan powder, 6.5 g (86%), mp 168°-170° C. dec. and further characterized by:

$^1$H NMR (CDCl$_3$) $\delta$2.40 (s, 3H), 2.44 (s, 6H), 2.75 (m, 4H), 3.30 (m, 4H), 4.28 (s, 4H), 7.27 (d, 2H), 7.34 (d, 4H), 7.43 (d, 2H), 7.65 (d, 4H), 7.75 (t, 1H); and $^{13}$C NMR δ21.48, 47.29, 50.37, 54.86, 124.19, 127.00, 127.11, 129.73, 135.04, 135.74, 138.95, 143.42, 143.73, 155.15.

Example C

Preparation of 3,6,9,15-tetraazabicyclo[9.3.1]pentadeca-1(15),11,13-triene.

A solution of HBr and AcOH was prepared by mixing 48% HBr and glacial AcOH in a 64.35 ratio. To 112 mL of the HBr/AcOH mixture was added 5.5 g (8.2 mmol) of 3,6,9-tris(p-tolylsulfonyl)-3,6,9,15-tetraazabicyclo[9.3.1]pentadeca-1(15),11,13-triene (prepared by the procedure of Example B) and the reaction mixture was heated at mild reflux with constant stirring for 72 hrs. The reaction mixture was then cooled to room temperature and concentrated to approximately 1/10 of the original volume. The remaining solution was stirred vigorously and 15–20 mL of diethyl ether was added. An off-white solid formed which was filtered, washed with diethyl ether, and dried in vacuo. The dry tetrahydrobromide salt was then dissolved in 10 mL of water, adjusted to pH 9.5 with NaOH (50% w/w) and continuously extracted with chloroform for 4 hrs. After drying over anhydrous sodium sulfate, the chloroform was evaporated to give a light-tan oil which gradually crystallized upon standing at room temperature to yield 1.2 g (71%) of the title product, mp 86°–88° C. and further characterized by:

$^1$H NMR (CDCl$_3$) δ2.21 (m, 4H), 2.59 (m, 4H), 3.06 (s, 3H), 3.85 (s, 4H), 6.89 (d, 2H), 7.44 (t, 1H); and $^{13}$C NMR δ48.73, 49.01, 53.63, 119.67, 136.29, 159.54.

FINAL PRODUCTS

Example 1

Preparation of 3,6,9,15-tetraazabicyclo[9.3.1]pentadeca-1(15),11,13-triene-3,6,9-trimethylenephosphonic acid (PCTMP).

A mixture of 2.06 g (10 mmol) of 3,6,9,15-tetraazabicyclo[9.3.1]pentadeca-1(15),11,13-triene (prepared by the procedure of Example C), 11.3 g (138 mmol) of phosphoric acid and 15 g (152 mmol) of concentrated HCl was heated to gentle reflux (103° C.) with constant stirring followed by the dropwise addition (2 mL/min) of 12.2 g (150 mmol, 15 mL) of aqueous formaldehyde (37%). After complete addition, the reaction mixture was stirred at reflux for 16 hrs, cooled to room temperature and concentrated to a thick, viscous oil. The product was then purified by LC anion exchange chromatography (0–30% formic acid, 3 mL/min, retention time=32 min). The combined fractions were freeze-dried to give 4.8 g (99%) of the title product as a white solid, mp 275°–280° C. and further characterized by:

$^1$H NMR (D$_2$O) δ2.83 (m, 6H), 3.46 (m, 10H), 7.28 (d, 2H), 7.78 (t, 1H); and $^{13}$C NMR δ53.61, 53.81, 55.27, 57.93, 62.20, 125.48, 143.08, 152.31; and $^{31}$P NMR δ8.12 (2P), 19.81 (1P).

Example 2

Preparation of the complex of $^{153}$Sm-3,6,9,15-tetraazabicyclo[9.3.1]pentadeca-1(15),11,13-triene-3,6,9-trimethylenephosphonic acid ($^{153}$Sm-PCTMP)

A solution of the ligand of Example 1 was prepared by dissolving 3.8 mg of ligand/0.517 mL of deionized water (pH=2). A 1:1 ligand/metal complex was then prepared by combining 40 μl of the ligand solution with 2 mL of aqueous SmCl$_3$·H$_2$O ($3\times10^{-4}$M in 0.1N HCl) containing tracer $^{153}$SmCl$_3$. After thorough mixing, the percent metal as a complex was determined by passing a sample of the complex solution through a Sephadex™ column, eluting with 4:1 saline (0.85% NaCl/NH$_4$OH), and collecting 2×3 mL fractions. The amount of radioactivity in the combined elutions was then compared with that left on the resin. Under these conditions, complex was removed with the eluent and non-complexed metal is retained on the resin. By this method complexation was determined to be 98%. A sample of the solution that was passed through the resin was used for pH studies. The pH stability was then determined using the General Procedure above.

Example 3

Preparation of the complex of $^{166}$Ho-3,6,9,15-tetraazabicyclo[9.3.1]pentadeca-1(15),11,13-triene-3,6,9-trimethylenephosphonic acid ($^{166}$Ho-PCTMP)

When the procedure of Example 2 was repeated using $^{166}$HoCl$_3$ in place of $^{153}$SmCl$_3$, the title product was obtained.

Example 4

Preparation of the complex of $^{90}$Y-3,6,9,15-tetraazabicyclo[9.3.1]pentadeca-1(15),11,13-triene-3,6,9-trimethylenephosphonic acid ($^{90}$Y-PCTMP)

When the procedure of Example 2 was repeated using $^{90}$YCl$_3$ in place of $^{153}$SmCl$_3$, the title product was obtained.

BIODISTRIBUTION

General Procedure

Sprague Dawley rats were allowed to acclimate for five days then injected with 100 μl of the complex solution via a tail vein. The rats weighed between 150 and 200 g at the time of injection. After 30 min. the rats were killed by cervical dislocation and dissected. The amount of radioactivity in each tissue was determined by counting in a NaI scintillation counter coupled to a multi-channel analyzer. The counts were compared to the counts in 100 μl standards in order to determine the percentage of the dose in each tissue or organ.

The percent dose in blood was estimated assuming blood to be 7% of the body weight. The percent dose in bone was estimated by multiplying the percent dose in the femur by 25. The percent dose in muscle was estimated assuming muscle to be 43% of the body weight.

EXAMPLE I

The percent of the injected dose of complex of Example 2 ($^{153}$Sm-PCTMP) in several tissues are given in Table I. The numbers represent the average of 5 rats per data point.

TABLE I

| % INJECTED DOSE IN SEVERAL TISSUES FOR $^{153}$Sm-PCTMP | |
|---|---|
| Tissue | Average |
| Bone | 60 |
| Liver | 2.80 |
| Kidney | 0.38 |
| Spleen | 0.16 |
| Muscle | 0.40 |
| Blood | 0.29 |

EXAMPLE II

The percent of the injected dose of the complex of $^{166}$Ho with the ligand of Example 1 (PCTMP), prepared in Example 3, in several tissues are given in Table II. The numbers represent the average of 3 rats per data point.

TABLE II

| % INJECTED DOSE IN SEVERAL TISSUES FOR $^{166}$Ho-PCTMP | |
| --- | --- |
| Tissue | Average |
| Bone | 43 |
| Liver | 3.55 |
| Kidney | 0.33 |
| Spleen | below background |
| Muscle | 0.34 |
| Blood | 0.12 |

EXAMPLE III

The percent of the injected dose of complex of $^{90}$Y with the ligand of Example 1 (PCTMP), prepared in Example 4, in several tissues are given in Table III. The numbers represent the average of 3 rats per data point.

TABLE III

| % INJECTED DOSE IN SEVERAL TISSUES FOR $^{90}$Y-PCTMP | |
| --- | --- |
| Tissue | Average |
| Bone | 29 |
| Liver | 0.21 |
| Kidney | 0.36 |
| Spleen | below background |
| Muscle | 0.42 |
| Blood | 0.18 |

The bone to blood ratio (% dose/G) was 140. The bone to liver ratio was 76. The bone to muscle ratio was 400.

EXAMPLE IV

The complex of $^{153}$Sm with the ligand of Example 1 (PCTMP) had a bone localization of about 60% at a 5:1 ligand to metal ratio. This result suggests that the reduced charge chelate could deliver specifically to bone.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A complex which comprises a bicyclopolyazamacrocyclophosphonic acid compound of the formula

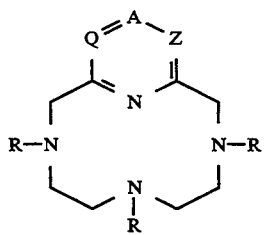

wherein:

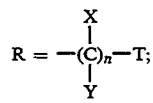

where:
X and Y are independently H, OH, C$_1$-C$_3$ alkyl or COOH;
n is an integer of 1, 2 or 3;
with the proviso that: when n is 2, then the sum of X and Y must equal two or more H; and when n is 3, then the sum of X and Y must equal three or more H; T is

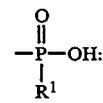

where:
R$^1$ is OH or C$_1$-C$_5$ alkyl;
with the proviso that at least one T must be P(O)R$^1$OH where R$^1$ is C$_1$-C$_5$ alkyl;

A is CH, N, C—Br, C—Cl, C—OR$^3$, C—OR$^8$, N$^+$—R$^5$ X$^-$,

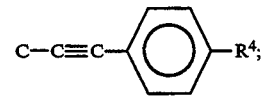

R$^3$ is H, C$_1$-C$_5$ alkyl, benzyl, or benzyl substituted with at least one R$^4$;
R$^4$ is H, NO$_2$, NH$_2$, isothiocyanato, semicarbazido, thiosemicarbazido, maleimido, bromoacetamido or carboxyl;
R$^5$ is C$_1$-C$_{16}$ alkyl, benzyl, or benzyl substituted with at least one R$^4$;
R$^8$ is C$_1$-C$_{16}$ alkylamino;
X$^-$ is Cl$^-$, Br$^-$, I$^-$ or H$_3$CCO$_2^-$;
Q and Z independently are CH, N, N$^+$—R$^5$ X$^-$, C—CH$_2$—OR$^3$ or C—C(O)—R$^6$;
R$^3$ and R$^5$ are defined as above;
R$^6$ is —O—(C$_1$-C$_3$ alkyl), OH or NHR$^7$;
R$^7$ is C$_1$-C$_5$ alkyl or a biologically active material;
X$^-$ is defined as above; or
pharmaceutically-acceptable salts thereof;
with the proviso that:
a) when Q, A or Z is N or N$^+$—R$^5$ X$^-$, then the other two groups must be CH;
b) when A is C—Br, C—Cl, C—OR$^3$ or C—OR$^8$, then both Q and Z must be CH;
c) the sum of the R$^4$, R$^7$ and R$^8$ terms, when present, may not exceed one; and
d) only one of Q or Z can be C—C(O)—R$^6$ and when one of Q or Z is C—C(O)—R$^6$, then A must be CH;
complexed with a metal ion of $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{99m}$Tc, $^{67}$Ga, $^{68}$Ga, $^{105}$Rh, $^{97}$Ru, $^{111}$In, $^{113m}$In or $^{115m}$In.

2. A complex of claim 1 wherein the metal is $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{142}$Pr, $^{99m}$Tc, $^{67}$Ga, $^{68}$Ga, $^{111}$In, $^{113m}$In or $^{115m}$In.

3. A complex of claim 2 wherein the metal ion is $^{153}$Sm, $^{177}$Lu, $^{166}$Ho, $^{90}$Y, $^{99m}$Tc, $^{67}$Ga, $^{68}$Ga, $^{111}$In, $^{113m}$In or $^{115m}$In.

4. A complex of claim 3 wherein the metal ion is $^{153}$Sm, $^{177}$Lu or $^{166}$Ho.

5. A complex of claim 1 wherein at least two R terms have T equal to P(O)R$^1$OH, where R$^1$ is OH, and in the third R term T is P(O)R$^1$OH, where R$^1$ is C$_1$–C$_5$ alkyl; A, Q and Z are CH; n is 1; and X and Y independently are H or C$_1$–C$_3$ alkyl.

6. A complex of claim 1 wherein at least one R term has T equal to P(O)R$^1$OH, where R$^1$ is OH, and in the other two R terms, T is P(O)R$^1$OH, where R$^1$ is C$_1$–C$_5$ alkyl, X and Y are H; A, Q and Z are CH; and n is defined as in claim 1.

7. A complex of claim 1 wherein three R terms have T equal to P(O)R$^1$OH, where R$^1$ is C$_1$–C$_5$ alkyl; n is defined as in claim 1; X and Y are H; and A, Q and Z are CH.

8. A complex of claim 1 wherein X and Y are H.

9. A complex of claim 1 wherein n is 1.

10. A complex of claim 1 wherein A, Q and Z are CH.

* * * * *